(12) United States Patent
Boutilier et al.

(10) Patent No.: US 10,966,381 B2
(45) Date of Patent: Apr. 6, 2021

(54) HAPLOID EMBRYOGENESIS

(71) Applicant: STICHTING WAGENINGEN RESEARCH, Wageningen (NL)

(72) Inventors: Kimberly Boutilier, De Meern (NL); Gerrit Cornelis Angenent, Wageningen (NL); Mercedes Soriano Castan, Monzon (ES); Li Hui, Beijing (CN)

(73) Assignee: STICHTING WAGENINGEN RESEARCH, Wageningen (NL)

( * ) Notice: Subject to any disclaimer, the term of this patent is extended or adjusted under 35 U.S.C. 154(b) by 444 days.

(21) Appl. No.: 15/024,296

(22) PCT Filed: Sep. 24, 2014

(86) PCT No.: PCT/EP2014/070367
§ 371 (c)(1),
(2) Date: Mar. 24, 2016

(87) PCT Pub. No.: WO2015/044199
PCT Pub. Date: Apr. 2, 2015

(65) Prior Publication Data
US 2016/0212956 A1   Jul. 28, 2016

(30) Foreign Application Priority Data

Sep. 24, 2013 (WO) ................. PCT/EP2013/069851

(51) Int. Cl.
| | | |
|---|---|---|
| A01H 4/00 | (2006.01) | |
| A01H 1/00 | (2006.01) | |
| A01H 1/08 | (2006.01) | |
| A01N 37/28 | (2006.01) | |

(52) U.S. Cl.
CPC ............. *A01H 4/008* (2013.01); *A01H 1/00* (2013.01); *A01H 1/08* (2013.01); *A01N 37/28* (2013.01)

(58) Field of Classification Search
None
See application file for complete search history.

(56) References Cited

U.S. PATENT DOCUMENTS 6,544,957 B2 * 4/2003 Kern ................. A61K 45/06
514/44 R

FOREIGN PATENT DOCUMENTS

| WO | 2000054574 A2 | 9/2000 |
| WO | 2002052926 A2 | 7/2002 |

OTHER PUBLICATIONS

Burli et al (2013, "Design, Synthesis, and Biological Evaluation of Potent and Selective Class IIa Histone DSL (HDAC) Inhibitors As a Potential Therapy for Huntington's Disease", Journal of Medicinal Chemistry, 56:9934-9954).*
Touraev et al (1997, "Initiation of Microspore Embryogenesis by Stress", Trends in Plant Science, 2(8):297-302).*
Tanaka et al (2008, "The *Arabidopsis* Histone Deacetylases HDA6 and HDA19 Contribute to the Repression of Embryogenic Properties after Germination", Plant Physiology 146:149-161).*
Flora & Pachauri (2010) Int. J Environ Res Public Health, 7:2745-2788.*
Maraschin et al. (2005) J Exp Bot 56(417):1711-26.*
Bora-Tatar et al. (2009) Bioorg Med Chem 17:5219-28.*
Burli et al. (2013) J Med Chem 56:9934-54.*
Flora & Pachauri (2010) Int. J Environ Res Public Health, 7, 2745-88.*
Li, H. et al., The Histone Deacetylase Inhibitor Trichostatin A Promotes Totipotency in the Male Gametophyte, The Plant Cell, 26, 195-209, 2014.
PCT/EP2013/069851, International Search Report and Written Opinion, dated Jun. 24, 2014.
PCT/EP2014/070367, International Search Report and Written Opinion, dated Oct. 31, 2014.
Soriano, M. et al., Microspore Embryogenesis: Establishment of Embryo Identity and Pattern in Culture, Plant Reprod, 26, 181-196, 2013.
Tanaka, M. et al., The *Arabidopsis* Histone Deacetylases HDA6 and HDA19 Contribute to the Repression of Embryonic Properties After Germination, Plant Physiology, 146, 149-161, 2007.
Touraev, A. et al., Initiation of Microspore Embryogenesis by Stress, Trends in Plant Science, 2(8), 297-302, 1997.
Galinha, C. et al., Plethora Proteins as Dose-Dependent Master Regulators of *Arabidopsis* Root Development, Nature 449, 1053-1057, 2007.
Lopez-Molina, L. et al., A Postgermination Developmental Arrest Checkpoint is Mediated by Abscisic Acid and Requires the ABI5 Transcription Factor in *Arabidopsis*, PNAS 98(8), 4782-4787, 2001.
Lopez-Molina, L. et al., ABI5 Acts Downstream of ABI3 to Execute an ABA-Dependent Growth Arrest During Germination, The Plant Journal 32, 317-328, 2002.
Malik, M. et al., Transcript Profiling and Identification of Molecular Markers for Early Microscope Embryogenesis in *Brassica napus*, Plant Physiology 144, 134-154, 2007.

(Continued)

*Primary Examiner* — Russell T Boggs
(74) *Attorney, Agent, or Firm* — Global Patent Group, LLC; Dennis Bennett; Clifford Schlecht

(57) ABSTRACT

A switch to haploid embryogenesis is controlled by the activity of histone deacetylases (HDACs). Blocking HDAC activity with HDAC inhibitors (HDACi), e.g. trichostatin A (TSA), in *Brassica napus, B. rapa, B. oleracea, Arabidopsis thaliana* and *Capsicum annuum* male gametophytes leads to a large increase in the proportion of cells that undergo embryogenic growth. In *B. napus*, treatment with one specific HDACi (SAHA) improves the conversion (i.e. germination) of these embryos into seedlings. Existing methods of culturing microspores of angiosperm plants following stress to produce haploid embryos, haploid plants and double haploid plants can be improved by adding HDACi to the culture medium. Advantageously, species hitherto recalcitrant to haploid embryogenesis via microspore culture are rendered useful when using HDACi. Haploid and double haploid plants are of industrial application in the plant breeding programmes.

3 Claims, 16 Drawing Sheets

(56) References Cited

OTHER PUBLICATIONS

Santos-Mendoza, M. et al., Deciphering Gene Regulatory Networks That Control Seed Development and Maturation in *Arabidopsis*, The Plant Journal 54, 608-620, 2008.

Zhang, H. et al., An Epigenetic Perspective of Developmental Regulation of Seed Genes, Molecular Plant 2(4), 610-627, 2009.

Marks, P. et al., "Histone Deacetylase Inhibitors: Inducers of Differentiation or Apoptosis of Transformed Cells", J Natl Cancer Inst, 92(15):1210-1216, (2000).

* cited by examiner

| compounds | concentration (µM) | embryo morphology | | | |
|---|---|---|---|---|---|
| | | 1 | 2 | 3 | 4 |
| DMSO | 0.05 | T | ℓ | ◠ | ○ |
| | 0.5 | T | ℓ | ◠ | ○ |
| | 5 | T | ℓ | ◠ | ○ |
| SAHA | 0.05 | T | ℓ | ◠ | ○ |
| | 0.5 | T | ℓℓ | ◠ | ○ |
| | 5 *** | T | TTTT | ℓℓℓ | ◠ |
| TSA | 0.05 *** | T | ℓℓℓℓℓ | TTTTT | ◠◠ |
| | 0.5 | --- | --- | ( | ( |
| | 5 | --- | --- | --- | --- |
| scriptaid | 0.05 | T | ℓℓ | ◠ | ○ |
| | 0.5 *** | T | TTTTT | ℓ | ◠ |
| | 5 | T | T | TT | ◠◠ |

T  0.1% embryos

HAPLOID EMBRYOGENESIS

This application claims the benefit of priority under 35 U.S.C. § 371 of PCT International Application No. PCT/EP2014/070367, filed Sep. 24, 2014, which in turn claims the benefit of priority to PCT International Application No. PCT/EP2013/069851, filed Sep. 24, 2013, which is incorporated herein by reference in its entirety.

TECHNICAL FIELD

The invention relates to the field of plant breeding and in particular the generation and making of haploid or doubled haploid (DH) plants. More particularly the invention concerns the physico-chemical induction of haploid embryos from plant gametophytes and the conversion of such embryos into plantlets.

BACKGROUND ART

Many plant cells have the inherent ability to regenerate a complete organism from single cells or tissues, a process referred to as totipotency. During sexual reproduction, cellular totipotency is restricted to the zygote, which is formed in the seed from fusion of the egg and sperm cells upon fertilisation. Sustained division of the zygote generates the embryo, which contains the basic body plan of the adult plant. Establishment of groups of pluripotent stem cells in the stem cell niche of the embryonic shoot and root apical meristems ensures the continuous post-embryonic growth and development of new lateral organs that is characteristic for plant development (see Bennett, T., and Scheres, B. (2010) Curr. Top. Dev. Biol. 91: 67-102 and Besnard, F., et al. (2011) Cell. Mol. Life Sci, 68: 2885-2906).

Embryo development also occurs in the absence of egg cell fertilisation during apomixis, a type of asexual seed development. Totipotency in apomictic plants is restricted to the gametophytic and sporophytic cells that normally contribute to the development of the seed and its precursors, including the unfertilised egg cell and surrounding sporophytic tissues (see Bicknell, R. A., and Koltunow, A. M. (2004) Plant Cell 16: S228-S245).

The totipotency of plant cells reaches its highest expression in tissue culture. The ability of a cell to undergo embryogenesis in vitro is both an inherent and an acquired characteristic that requires the right combination of explant and culture environment. A wide variety of cells have the potential to develop into embryos, including haploid gametophytic cells, such as the cells of pollen and embryo sacs (see Forster, B. P., et al. (2007) Trends Plant Sci, 12: 368-375 and Seguí-Simarro, J. M. (2010) Bot. Rev. 76: 377-404), as well as somatic cells derived from all three tissue layers of the plant (Gaj, M. D. (2004) Plant Growth Regul, 43: 27-47 or Rose, R., et al. (2010) "Developmental biology of somatic embryogenesis" in: Plant Developmental Biology-Biotechnological Perspectives, P. E-C and D. MR, eds (Berlin Heidelberg: Springer), pp. 3-26).

The treatments used to induce embryogenesis are diverse and range from application of exogenous growth regulators to abiotic stress. Under the appropriate conditions; the explant resumes cell division and produces histodifferentiated embryos, either directly from the explant or indirectly from callus. The morphological and cellular changes that occur during in vitro embryogenesis have been described in some species (Raghavan, V. (2004) Am. J. Bot. 91: 1743-1756; Seguí-Simarro, J. M., and Nuez, F. (2008) Physiol. Plant. 134: 1-12), but there is still very little known about the initial steps involved in the acquisition and expression of totipotency in individual cells, and many of the assumed diagnostic features of cultured embryogenic cells are being revised in the light of live imaging studies (Daghma, D., et al. (2012) J. Exp. Bot. 63: 6017-6021; Tang; X.; et al. (2013) J. Exp. Bot. 64: 215-228.

Molecular screens have been performed to identify the changes that occur during in vitro embryogenesis, however the range of species, explants and culture conditions that have been used, combined with low percentage of cells that form embryos, has made it difficult to develop a unified concept of the totipotent plant cell.

In *Arabidopsis*, dynamic regulation of gene expression at the chromatin level has been shown to play a major role in translating the developmental and environmental signals that regulate plant cell totipotency in planta (Zhang, H., & ©gas, J. (2009) Mol. Plant 2: 610-627.

The basic structural and functional unit of chromatin is the nucleosome, which comprises DNA wrapped around a histone octamer, and associated linker histones. Nucleosomes can represent a physical barrier to DNA for non-histone proteins due to the strong interaction between the positively charged histones and negatively charged DNA. Transcription requires physical binding of transcription factors to open DNA; thus, controlling the compaction and accessibility of loci through nucleosomes offers a dynamic means to control gene expression. Dynamic changes in chromatin structure and gene transcription are mediated primarily by the interwoven processes of chromatin remodelling and histone modification. Chromatin remodelling proteins use the energy from ATP hydrolysis to remove or reposition nucleosomes, while histone modifying enzymes chemically modify lysines and other amino acids on the exposed N-terminal tails of histones to change their charge and interaction with DNA and other proteins.

In plants, a number of conserved chromatin modifying proteins ensure the successful transition from embryo development to post-embryonic growth by repressing pathways controlling embryo cell proliferation and identity during germination. Loss-of-function mutants of these proteins ectopically express embryo identity genes and produce somatic embryos from seedlings. These chromatin modifying proteins include members of the *Arabidopsis* SWI/SNF and CHD class of chromatin-remodelling ATPases (Ogas, J., et al. (1999) Proc. Natl. Acad. Sci. USA 96: 13839-13844), members of the Polycomb Group (PcG) Repressive Complex 1 (PRC1) and 2 (PRC2), which deposit repressive marks on histones, respectively, histone 2A lysine 119 (H2AK119) ubiquitination and histone 3 lysine 27 (H3K27) trimethylation (see Chanvivattana, Y., et al. (2004) Development 131: 5263-5276; Schubert, D., et al. (2005) Curr. Opin. Plant Biol, 8: 553-561; Makarevich, G., et al. (2006) EMBO Rep. 7: 947-952; Chen, Z., et al. (2009) Proc. Natl. Acad. Sci. USA 106: 7257-7262; Bratzel, F., et al, (2010) Curr. Biol. 20: 1853-1859; Bouyer, D., et al. (2011) PLoS Genet. 7: e1002014; Tang, X., et al. (2012) J. Exp. Bot. 63: 1391-1404). The large number of proteins that play a role in this process, combined with the potential cross-talk between different chromatin modifying proteins (Zhang, H., et al. (2012) Plant Physiol. 159: 418-432) ensures a multi-level dynamic control over cell totipotency.

Changes in chromatin organisation and modification are often associated with in vitro plant regeneration (Miguel, C., & Marum, L. (2011) J. Exp. Bot. 62: 3713-3725, but there are few examples where chromatin level changes are known to play a direct role in this process (He, C., et al. (2012) PLoS Genet. 8: e1002911).

Haploid embryogenesis was initially described almost 50 years ago in *Datura stramonium* (Guha, S., & Maheshwari, S. (1964) Nature 204: 497. The ability of haploid embryos to convert spontaneously or after treatment with chromosome doubling agents to doubled-haploid plants is widely exploited as a means to generate homozygous plants in a single generation, and has numerous breeding and trait discovery applications (Touraev, A., et al. (1997) Trends Plant Sci. 2: 297-302; Forster et al. (2007) supra). Haploid embryo production from cultured immature male gametophytes is a widely used plant breeding and propagation technique.

The haploid multicellular male gametophyte of plants, the pollen grain, is a terminally differentiated structure whose function ends at fertilization. Unlike mature gametophyte, the immature gametophyte retains its capacity for totipotent growth when cultured in vitro. When cultured in vitro an immature gametophyte can be induced to form haploid embryos. This way of forming haploid embryos was described nearly 50 years ago, but one that is poorly understood at the mechanistic level.

Haploid embryo development (also referred to as microspore embryogenesis, pollen embryogenesis or androgenesis) is induced by exposing anthers or isolated gametophytes to abiotic or chemical stress during in vitro culture (see Touraev, A., et al (1997) Trends Plant Sci. 2: 297-302. These stress treatments induce sustained division of the gametophyte leading to the formation of a histodifferentiated haploid embryo.

*Brassica* napes is one of the most well studied models for microspore embryogenesis (see Ousters, J. B. M., et al, (2001) Current trends in the embryology of angiosperms. In: Androgenesis in *Brassica*, a model system to study the initiation of plant embryogenesis, S. S. Bhojwani and W. Y. Soh, eds (Dordrecht: Kluwer Academic Publishers), pp. 451-470). A heat-stress treatment is used to induce microspore embryogenesis in this and other *Brassica* species. Only a small percentage of the heat-stressed immature male gametophytes will develop into differentiated embryos, although the number of sporophytically-dividing cells may be initially much higher.

Microspore-derived embryogenesis is a unique process in which haploid, immature pollen (microspores) are induced by one or more stress treatments to form embryos in culture. These microspore-derived embryos (MDEs) can be germinated and converted to homozygous doubled haploid (DH) plants by chromosome doubling agents and/or through spontaneous doubling. DH production is a major tool in plant breeding and trait discovery programs as it allows homozygous lines to be produced in a single generation. This quick route to homozygosity not only drastically reduces the breeding period, but also unmasks traits controlled by recessive alleles. DHs are widely used in crop improvement as parents for F1 hybrid seed production, to facilitate backcross conversion, for mutation breeding, and to generate immortal populations for molecular mapping studies.

The morphological and cellular changes that occur during the induction and development of haploid embryos have been well described, however there is still very little known about the mechanisms underlying this process. Molecular screens have been performed to identify the changes that occur during the induction and growth of haploid embryos, however no specific genes or signalling pathways have been unequivocally identified as causal factors.

Many years of cell biological studies in model species such as tobacco, barley and *Brassica*, have laid a solid foundation for understanding the cellular events that accompany haploid embryogenesis, yet the mechanism underlying this change in developmental pathways is not known (see Mercedes S. et al., (2013) Plant Reprod. 26: 181-196).

Li, W-Z. et al, (2001) In Vitro Cell. Dev. Biol.-Plant 37: 605-608 describes the effects of DNA hypomethylating drugs azacytidine and ethionine on androgenesis in barley (*Hordeum vulgare* L.).

Furuta, K., et al. (2011) Plant Cell Physiol. 52: 618-628 is entitled "The CKH2/PKL chromatin remodelling factor negatively regulates cytokinin responses in *Arabidopsis* calli." Subject of this scientific work were two isolated mutants of *Arabidopsis thaliana*, ckh1 (cytokine hypersensitive 1) and ckh2. These mutants are cytokine hypersensitive and produce rapidly growing (diploid) green calli in response to lower levels of cytokines. The authors were looking for a mechanism behind the cytokinin-inducible callus greening. Trichostatin A (TSA) was found able to partially replace the growth regulator cytokinin in callus formation from hypocotyl segments, which usually requires auxin and cytokinin. The starting material and calli tested were all diploid. Such diploid calli are organized, rooty and organogenic.

Acetylation and deacetylation of the lysine residue in histone proteins are often involved in the reversible modulation of chromatin structure in eukaryotes and can mediate the positive-negative regulation of transcription. Histone acetyltransferase catalyzes histone acetylation. Histone deacetylase (HDAC) catalyzes histone deacetylation. Hitherto, a number of disparate and yet putative functions for HDACs in plants have been suggested in the scientific literature.

For example, Tanaka M, et al. (2008) Plant Physiol. 146: 149-61 reports on effects of HDAC inhibitor trichostatin A (TSA) on seed germination in *Arabidopsis*. Normally, *Arabidopsis* seeds show radicle emergence with cotyledon expansion and greening within about 7 days after sowing. In contrast, following treatment with TSA, most *Arabidopsis* seeds show radicle emergence, but no cotyledon expansion or greening. This is also associated with expression of embryo-specific factors and the formation of embryo-like structures. A TSA concentration-dependent post-germination growth arrest was observed, as well as formation of embryo-like structures after germination. The authors suggest a role for HDAC following germination in the repression of existing embryonic properties in *Arabidopsis*, but without indication as to any mechanism.

Although DH production is widely exploited, there are often one or more bottlenecks that need to be overcome before an efficient DH production system can be established for a specific crop or genotype. One major bottleneck is a low level of haploid embryo induction. Entire species are often recalcitrant, and even responsive species show a strong genotypic component for DH production. In non-responsive genotypes, the microspores either fail to divide or arrest early in their development. A second bottleneck is the low rate of embryo germination and conversion to plantlets, a phenomenon that has been attributed to poor meristem development.

Histone deacetylase inhibitors (HDACi) have a long history and have been used in psychiatry and neurology as mood stabilizers and anti-epileptics. More recently they are being investigated further in relation to possible treatments for inflammatory diseases and cancers.

DISCLOSURE OF THE INVENTION

The inventors have discovered that by using a chemical approach, the switch to haploid embryogenesis is controlled by the activity of histone deacetylases (HDACs). Blocking at least part of HDAC activity with an inhibitor of HDAC (HDACi) in cultured immature male gametophytes leads to a large increase in the proportion of cells that switch from pollen to embryogenic growth. Whilst not wishing to be bound by any particular theory, the inventors have found that HDACi used in microspore culture blocks an existing developmental program and causes switch to a new program.

The inventors also discovered that HDACi induced embryogenesis and growth may be enhanced by, but is not dependent on, other stress, such as high temperature stress.

The inventors have also discovered that the immature male gametophyte of a species recalcitrant for haploid embryo development in culture, also forms embryogenic cell clusters after HDAC inhibitor treatment.

Accordingly, the present invention provides a method of producing haploid plant embryos comprising culturing haploid plant material in the presence of a histone deacetylase inhibitor (HDACi). Culturing may include the growing of haploid material in the presence of HDACi.

The invention also includes a method of producing haploid seedlings comprising exposing haploid plant material to a histone deacetylase inhibitor (HDACi) to produce haploid embryos and then converting (i.e. germinating) the haploid embryos into seedlings.

The invention therefore includes a method of making haploid plants comprising growing a seedling produced in accordance with the aforementioned method.

The invention also provides a method of producing a double haploid plant comprising culturing haploid plant material in the presence of a histone deacetylase inhibitor (HDACi) for a period, stimulating or allowing a spontaneous chromosome doubling, and growing the double haploid plant material into a seedling, plantlet or plant.

In certain embodiments, haploid embryogenesis and chromosome doubling may take place substantially simultaneously. In other embodiments, there may be a time delay between haploid embryogenesis and chromosome doubling. The time delay may relate to the developmental stage reached by the growing haploid embryo, seedling or plantlet. Should growth of haploid seedlings, plants or plantlets not involve a spontaneous chromosome doubling event, then a chemical chromosome doubling agent may be used in accordance with procedures which the average skilled person will be familiar, see for example:

Various possibilities arise, including exposing haploid plant material to a histone deacetylase inhibitor (HDACi) until a stage is reached where at least one of: a haploid multicellular globular mass, a globular embryo, a torpedo embryo, an embryo with cotyledon(s) is formed, then growing the haploid plant material onwards from that stage in culture for a period of time to allow a spontaneous chromosome doubling, and regenerating the subsequent double haploid plant material in culture to form a seedling. Where a microspore is exposed to the HDACi, then once a sporophytic growth path is identifiable from, for example from one of the stages of symmetric division, multicellular globular mass or globular microspore derived embryo (MDE), heart embryo, torpedo embryo and then embryo with cotyledon(s), then HDACi exposure may be stopped and the sporophytic growth or embryo growth continued in suitable growth medium. The growth medium may simply be the same as during HDACi exposure, but without the HDACi present.

Each of the stages of symmetric division, multicellular globular mass are readily visualised under a microscope by a person of ordinary skill in this field of art. Similarly, each of the stages of or globular microspore derived embryo (MDE), heart embryo, torpedo embryo and then embryo with cotyledon(s) are readily visualised under a low power microscope by a person of ordinary skill in this field of art.

Where a microspore is exposed to the HDACi, then a callus may form and this may undergo organogenesis to form an embryo. The invention therefore includes a method of producing haploid plant callus comprising exposing haploid plant material to a histone deacetylase inhibitor (HDACi).

Without wishing to be bound by particular theory, the inventors identify two potential sporophytic pathways; one which produces compact embryos that remain enclosed in the exine until between about 5 to 7 days of culture. The other producing cells that emerge earlier from the exine and show varying degrees of cell connectedness. However, both pathways express embryo program genes. The invention therefore includes a method of producing a haploid plant comprising exposing haploid plant material to a histone deacetylase inhibitor (HDACi) to form a callus and regenerating a plant from the callus.

Without wishing to be bound by particular theory, the inventors believe that a different type of callus is formed after HDACi treatment of microspores than is formed during shoot or root organogenesis. This type of callus is non-rooty and embryogenic.

As described herein, the term "plant" includes a seedling. A plant may also be a plant at any stage of growth and development from seedling to mature plant.

The plant and therefore the plant gametophyte may be an angiosperm or a gymnosperm. When an angiosperm, then the plant may be a monocot or a dicot.

The exposure of plant material to HDACi is preferably carried out for a period of time sufficient to induce haploid embryo formation. Where the starting haploid material is a microspore, this period of time may be determined by the developmental stage reached, e.g. symmetric division, multicellular globular mass or globular microspore derived embryo (MDE), heart embryo, torpedo embryo and then embryo with cotyledon(s). The stage reached and therefore period of time needed may depend on the species of plant concerned and these are all readily ascertainable by a person of ordinary skill in the art.

Where microspores and subsequent sporophytic developmental stages are exposed to HDACi in accordance with the methods of the invention, then this may take place for a period of time or times measured in hours. For example, a number of hours in the range 1-24, or 2-24, or 3-24, or 4-24, or 5-24, or 6-24, or 7-24, or 8-24, or 9-24, or 10-24, or 11-24, or 12-24, or 13-24, or 14-24, or 15-24, or 16-24, or 17-24, or 18-24, or 19-24, or 20-24, or 21-24, or 22-24, or 23-24 hours. Alternatively, a number of hours in the range 1-23, or 1-22, or 1-21, or 1-20, or 1-19, or 1-18, or 1-17, or 1-16, or 1-15, or 1-14, or 1-13, or 1-12, or 1-11, or 1-10, or 1-9, or 1-8, or 1-7, or 1-6, or 1-5, or 1-4, or 1-3, or 1-2 hours. A preferred range of HDACi exposure is from about 1 to about 20 hours; more preferably from about 2 to about 20 hours.

The period of exposure with HDACi may be measured in terms of days. Though a duration of more than about a day may not necessarily result in greater frequency of haploid embryo formation, the number of days may be in the range of from about 1 day to about 2 days, about 1 day to about 3 days, from about 1 day to about 4 days. A longer number of days than 4 may be used if desired.

Once haploid embryos are formed and observable, at whatever desired stage, then the embryo may be transferred to a growth medium free of HDACi. The growth medium may be a liquid or a solid medium. The growth medium will contain all the necessary compounds and factors that are necessary for the maintenance and/or further growth of the haploid embryo. Generally, the growth medium may be based on standard growth media used for diploid embryos or for haploid embryos produced/derived from seed or tissue culture, subject to modification/optimisation of components for the particular plant species concerned. Modification of the composition of growth media is something well within the range of skill of a person of ordinary skill in the art.

The exposure of haploid plant material to HDACi may be to a single compound or a mixture of compounds. One or more different compounds may be used in combination, whether simultaneously, separately or sequentially.

When maintaining or growing haploid embryos of any stage, there may be a spontaneous doubling of chromosomes leading to production of a double haploid seedling. Spontaneous doubling may occur via a variety of mechanisms.

Often, a double haploid embryo and resultant seedling may be produced from a microspore or other stages and/or cells of the gametophyte by using a chromosome doubling agent; optionally wherein the chromosome doubling agent is comprised in a gas, solution or a solid and the microspore, sporophytic microspore stage, haploid embryo, haploid callus or structure is exposed for a period to the chromosome doubling agent. The doubling agent may be used at any time from embryogenesis onwards, right up until the stage of meiosis would occur. So, doubling agents may be used on whole plant parts, such as shoots or buds, for example.

In some embodiments of the invention, HDACi and chromosome doubling agent may be present together when the plant material is exposed to them. The specific timing and protocol for chromosome doubling in each species' haploid material is something that the person of average skill in the art may readily ascertain by trial and error.

In certain aspects of the invention, a physical stress is applied to the haploid plant material prior to its exposure to the HDACi. The physical stress may be any of temperature, darkness, light or ionizing radiation, for example. The light may be full spectrum sunlight, or one or more frequencies selected from the visible, infrared or uv spectrum. One or more physical stresses or combinations of stress may be used prior to exposure to the HDACi compound. The stresses may be continuous or interrupted (periodic); regular or random over time. When stresses are combined over time they may be simultaneous (coterminous or partly overlapping) or separate.

In preferred methods of the invention the prior physical stress is removed prior to exposure to the HDACi compound.

The physical stress may be heat, but any other stress treatment such as starvation or osmotic stress (e.g. mannitol) may be used. Other stress treatments include n-butanol or ethanol. A combination of stress treatments may be used whether separately or simultaneously and if separately then optionally sequentially. For example when a heat treatment is used it may be a temperature in the range 20° C.-43° C.; possibly in the range 21° C.-34° C. Depending on the species of plant selected, the prior heat treatment may be at 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40"C, 41° C., 42° C., or 43"C fora period of time.

For any given stress treatment, the period of time may be from about 5 minutes to about 5 days, or a period of time selected from about 10 minutes to about 4 days, from about 20 minutes to about 3 days, from about 30 minutes to about 2 days, from about 1 hour to about 1 day, or from about 2 hours to 12 hours.

The haploid plant material to be subjected to the methods and uses of the invention is preferably a gametophyte; preferably an immature male gametophyte (i.e. microspore, or vegetative, generative or sperm cells of the pollen grain). The male gametophyte material may be comprised in an anther and the anther is subject to any of the aforementioned methods of the invention.

The invention as described herein may also be applied to an immature or mature female gametophyte (i.e. the megaspore and its derivatives, including the egg cell, the polar nuclei, the central cell, the synergids, the antipodals). The female gametophyte material may be comprised in an ovule and the ovule is subject to any of the aforementioned methods of the invention.

As described herein, a "histone deacetylase inhibitor" (HDACi) is preferably a compound which is capable of interacting with a histone deacetylase and inhibiting its enzymatic activity, thereby reducing the ability of a histone deacetylase to remove an acetyl group from a histone. In some preferred embodiments, such reduction of histone deacetylase activity is at least about 50%, more preferably at least about 75%, and still more preferably at least about 90%. In other preferred embodiments, histone deacetylase activity is reduced by at least 95% and more preferably by at least 99%.

The histone deacetylase inhibitor may be any molecule that effects a reduction in the activity of a histone deacetylase. This includes proteins, peptides, DNA molecules (including antisense), RNA molecules (including RNAi and antisense) and small molecules. A protein may be an antibody, monoclonal, polyclonal or chimeric; and a peptide may be a fragment of such an antibody.

HDACi compounds suitable for use in accordance with any of the aforementioned methods and uses of the invention in all its aspects are well known and generally available from commercial sources. These include the following classes of compound: hydroxamic acids, cyclic tetrapeptides, aliphatic acids, benzamides, polyphenolics or electrophilic ketones. More detailed information about HDACi compounds is provided in the detailed description below.

In preferred aspects, the method and uses of the invention employ HDACi which is trichostatin A (TSA), butyric acid, a butyrate salt, potassium butyrate, sodium butyrate, ammonium butyrate, lithium butyrate, phenylbutyrate, sodium phenylbutyrate or sodium n-butyrate.

In certain preferred methods and uses, the HDACi is suberoylanilide hydroxamic acid (SAHA) and this advantageously improves the conversion (i.e. "germination") of haploid embryos or doubled haploid embryos into seedlings.

The methods of the invention are particularly suited to achieving improved haploid embryogenesis than methods involving physical stress alone. For example, subject to the species concerned, when microspores are subjected to a method of the invention and compared to a control where no HDACi is present, at least 10% more haploid embryos are formed. In certain species this may be at least 25% more, at least 50% more, at least 75% more, at least 100% more, or at least 200% more. In some species the number of haploid embryos may be more than 25% more, more than 50% more, more than 75% more, more than 100% more or more than 200% more. Plants where increased haploid embryo formation is of particular benefit are model systems of rapeseed (*Brassica napus*), tobacco (*Nicotiana tabacum*), barley (*Hordeum vulgare*) and wheat (*Triticum aestivum*).

The methods of the invention are also particularly suited to producing haploid embryos where this has not been possible successfully so far, whether scientifically or commercially. Methods of the invention may be applied particularly to such previously recalcitrant species such as a species or variety of a genus selected from *Arabidopsis*, e.g. *A. thaliana*, or *Solanum*, e.g. *S. esculentum*.

The invention also includes a histone deacetylase inhibitor (HDACi) as hereinbefore described, for use in haploid plant embryogenesis; i.e. generating haploid embryos from haploid plant material by exposing the haploid plant material to HDACi and/or growing the haploid plant material in the presence of HDACi.

Also, the invention includes a histone deacetylase inhibitor (HDACi) for use in producing double haploid plant material; particularly seedlings which are then grown on to form plantlets or plants. Such double haploid plant material is generated in part as a result of haploid plant material undergoing an embryogenic event due to exposure to and/or growth in presence of an HDACi.

The invention also provides a kit for performing a method of haploid embryogenesis in plants comprising a first container which includes a histone deacetylase inhibitor (HDACI) and a second container which includes a chromosome doubling agent. Such kits may include a set of instructions for using the HDACI and chromosome doubling agents. Either or both of the HDACI and doubling agents may be in a concentrated form and require dilution prior to use. The kit may further comprise solutions for the dilution of the HDACi and/or doubling agent stock solutions that the kit provides. The HDACi and/or doubling agents may be provided in dry form and solutions may be provided in the kit for making up solutions. The kit may be designed for use with a particular plant species material and include specific instructions.

The invention will now be described in more detail including by way of examples and with reference to the drawings in which:

DETAILED DESCRIPTION

Figure 1:
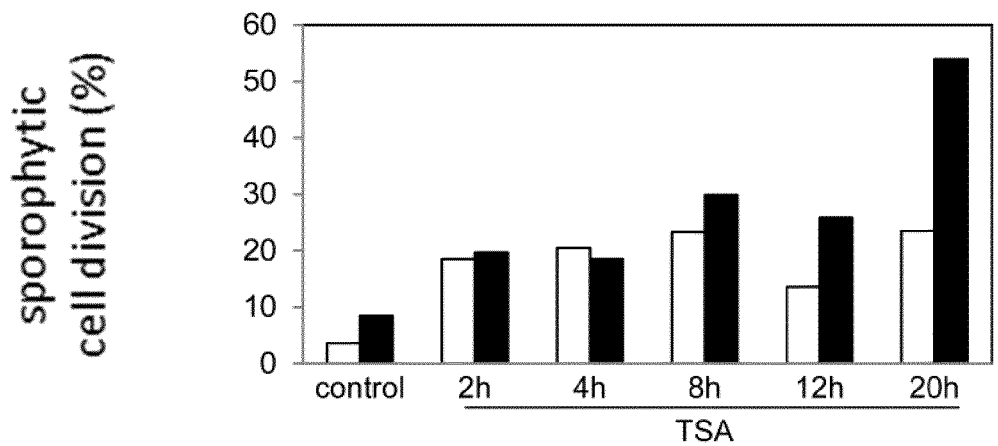
FIG. 1 is a bar chart of results showing the effect of the duration of TSA treatment on sporophytic cell division in *B. napus* DH12075 microspore culture.

The inventors have found that chemical inhibition of HDAC activity using trichostatin A (TSA) induces massive cell proliferation in the immature male gametophyte of *Brassica napus*, even in the absence of the heat stress treatment that is usually used to induce haploid embryogenesis. Using cell fate markers, the inventors have shown that the multicellular structures that develop after ISA treatment are embryogenic, but that most of these structures fail to form histodifferentiated embryos. Nonetheless, a higher embryo yield can be obtained after TSA treatment compared to untreated controls. TSA treatment is associated with increased acetylation of histones H3 and H4. Transcriptome analysis suggests that activation of cell cycle-, auxin signalling-, cell wall mobilisation- and embryo gene expression pathways contribute to the observed phenotypes.

Using a chemical approach, the inventors have found that the switch to haploid embryogenesis is controlled by the activity of histone deacetylases (HDACs), Blocking HDAC activity with HDAC inhibitors, e.g. TSA, in *Brassica napus, B. rapa, Arabidopsis thaliana* and *Capsicum annuum* male gametophytes leads to a large increase in the proportion of cells that undergo embryogenic growth. In *B. napus*, treatment with one specific HDACi (SAHA) improves the conversion (i.e. germination) of these embryos into seedlings.

The inventor's discovery of the utility of HDAC inhibitors for haploid embryogenesis can be used to produce and propagate new plant varieties, but will not be directly incorporated as traits per se in plants. For plant varieties in which DH production is possible, but inefficient, the invention will significantly increase the efficiency and decrease the cost of DH production, but will not have a significant impact on the cost of breeding new plants. The main value to be gained for these crops lies in the increased number of new DH lines or crosses from a breeding program that can be generated. All tested species so far react in the same way and so the present invention is also generically applicable, including to those plant species or varieties where DH production has not yet been achieved. Advantageously, this avoids having to develop tailor-made approaches for each crop/variety.

The inventors have shown that inhibition of histone deacetylation is sufficient to induce haploid embryo development in cultured pollen of both B, napus and *Arabidopsis*. Many different stressors can be used to induce haploid embryogenesis. In this respect, the deregulation of HDACs by stress and the accompanying changes in histone acetylation status provides a single, common regulation point for the induction of haploid embryogenesis.

The developmental stage of the vegetative cell plays a major role in its responsiveness to stress and TSA. In the majority of species, the stress treatment is most effective in triggering sustained cell division in culture shortly before or after PM I (Touraev et at (1997) supra). Heat-stressed *B. napus* microspores can be induced to divide sporophytically when they are at the G1 to G2 phase of the cell cycle, while the vegetative cell of the binucleate pollen is responsive, albeit at a much lower frequency, at G1 (Binarova, P., et al. (1993) Theor. Appl. Genet. 87: 9-16). During normal pollen development the vegetative cell does not divide after PM I and is assumed to arrest in G1 (G0). This stage of pollen development is much less responsive for haploid embryo induction. Unlike heat stress alone, TSA, alone or in combination with heat-stress, is highly effective at this late stage of pollen development, and has a much stronger effect than heat-stress alone with respect to the proportion of cells that divide sporophytically. TSA is a more potent inducer of sporophytic growth due to its ability to more completely inhibit individual HDACs or to inhibit a wider range of HDACs than heat-stress alone. The inventors have found that a relatively high concentration of TSA in combination with heat stress enhances divisions that mainly result in disorganized embryogenic structures, while a relatively low concentration of TSA in combination with heat-stress more closely mimics the effect of heat-stress alone in that the formation of both histodifferentiated embryos and non-viable disorganized embryogenic structures is enhanced.

Culture at lower temperatures dampens the effect of TSA, such that fewer cells divide, and a higher concentration of ISA is needed to induce embryo and embryogenic cell formation than at 33° C. In line with this observation, in *B. napus* a more severe, 41° C. heat-stress required to induce sporophytic divisions and embryogenesis at the late bicellular stage (Binarova, P., et al. (1997) Sex. Plant Reprod. 10: 200-208). HDACs (directly or indirectly) mediate the inhibition of cell cycle progression that is gradually imposed on the vegetative cell, and that release of this inhibition is required for embryogenic growth in culture.

The invention provides tools that can be immediately and easily applied by plant breeders in a GMO-free manner. The ability to use small compounds to improve tissue culture responses eliminates the need to create and market transgenic plants, allowing rapid and cost-effective innovation. This is important in the food sector, where consumers are hesitant about consuming transgenic products. A non-transgenic approach is also important when companies have crops/varieties with a small market share, for which the costs involved in developing and marketing transgenic plants are prohibitive.

A way of determining whether a compound is an HDACi for use in accordance with any of the aspects or embodiments of the invention is by using standard enzymatic assays derived from measuring the ability of an agent to inhibit catalytic conversion of a substance by the subject protein. In this manner, inhibitors of the enzymatic activity of histone deacetylase proteins can be identified (see Yoshida, et at, J. Biol Chem. 265: 17174-17179 (1990)).

More particularly, an HDACi for use in accordance with any of the aspects or embodiments of the invention described herein includes: trichostatin A (TSA) and compounds related to TSA, such as butyric acid, butyrate salts such as potassium butyrate, sodium butyrate, ammonium butyrate, lithium butyrate, phenylbutyrate, sodium phenylbutyrate (NaPBA); also sodium n-butyrate. Also, M344 which is an amide analog of TSA and analogues disclosed in US2011/0237832.

HDACi compounds for stimulating haploid embryogenesis in accordance with the invention include: suberoyl bis-hydroxamic acid (SBHA), vorinostat (suberoylanilide hydroxamic acid (SAHA)); valproic acid sodium salt (sodium valproate); Scriptaid (6-(1,3-Dioxo-1H, 3H-benzo[de] isoquinolin-2-yl)-hexanoic acid hydroxyamide) (see U.S. Pat. No. 6,544,957).

Also, rocilinostat (ACY-1215); etinostat (MS-275); mocetinostat (MGCD0103, MG0103); belinostat (PXD101); dacinostat (LAQ824); droxinostat (CMH, 5809354); resminostat (RAS2410); panobinostat (LBH589); pracinostat (SB939); givinostat (ITF2357); quisinostat (JNJ-26481585); abexinostat (PCI-24781).

Additionally, Trapoxin; specifically trapoxin A (Cyclo ((S)-phenylalanyl-(S)-phenylalanyl-(R)-pipecolinyl-(2S, 9S)-2-amino-8-oxo-9,10-epoxydecanoyl) and cyclic tetra-peptide compounds related to trapoxin A having the amino acid-2-amino-8oxo-9,10-epoxy-decanoic acid in their molecules, e.g. chlamydocin (Closse, et al., Helv. Chim. Acta 57: 533-545 (1974)), HC-toxin (Liesch, et al., Tetrahedron 38: 45-48 (1982)); Cyl-2; and WF-3161 (Umehara, K. J. Antibiot 36: 478-483 (1983). Trapoxin B may be used.

The following HDACi compounds are also suitable for use in accordance with the invention: oxamflatin ((2E)-5-[3-(Phenylsulfonylamino)phenyl]-pent-2-en-4-ynohydroxamic acid); depsipeptides such as romidepsin and spiruchostatin A; hybrid polar compounds (HPCs), such as suberoylanilide hydroxamic acid (SAHA) and m-carboxycinnamic acid bishydroxamide (CBHA); apicidin (CycloR2S)-2-amino-8-oxodecanoyl-1-methoxy-L-tryptophyl-L-isoleucyl-(2R)-2-piperidinexcarbonyl]); depudecin (4,5:8,9-Dianhydro-1,2,6,7,11-pentadeoxy-D-threo-D-ido-undeca-1,6-dienitol); romidepsin; trapoxin; radicicol; cambinol 5-(2-Hydroxynaphthalen-1-ylmethyl)-6-phenyl-2-thioxo-2,3-dihydro-1H-pyrimidin-4-one; tubacin; tubastatin A HCl; resveratrol 3,4',5-Trihydroxy-trans-stilbene; split-omicin 1,2-Dihydro-3H-naphtho[2,1-b]pyran-3-one; tacedinaline (C1994); sulindac; PXD101; PTACH S-[6-(4-Phenyl-2-thiazolylcarbamoyl)hexyl] thioisobutyrate; CUDC 101 (7-[[4-(3-Ethynylphenylamino)-7-methoxyquinazolin-6-yl] oxy]-N-hydroxyheptanamide); MOCPAC (Benzyl (S)-[1-(4-methyl-2-oxo-2H-chromen-7-ylcarbamoyl)-5-propionylaminopentyl] carbamate): MC1568; PCI-34051; C1-994 (: 4-Acetylamino-N-(2'-aminophenyl)benzamide); CUDC-101; CUDC-907; LAQ 824; AR-42 (OSU-HDAC42); APHA Compound 8 (3-(1-Methyl-4-phenylacetyl-1H-2-pyrrolyl)-N-hydroxy-2-propenamide); BATCP (5)-[5-Acetylamino-1-(2-oxo-4-trifluoromethyl-2H-chromen-7-ylcarbamoyl)pentyl]carbamic acid tert-butyl ester; MGDCD0103; 8B939; CHR-2845; CHR-3996; 480-202; Sulforaphane; Kevetrin.

Amongst polyphenolic HDACi compounds, naturally occurring plant polyphenols having this activity may be used. For example, (−)-epigallocatechin-3-gallate (EGCG) and genistein (GEN) as well as oxidative methyleugenol (ME) metabolites.

Natural products with HDACi activity are available and may be used in accordance with the invention, including: curcumin, butyrate, diallyl disulphide, sulfopropane and parthenolide.

Other HDACi molecules may include proteins and peptides, including antibodies or fragments thereof, preferably monoclonal antibodies that specifically react with the histone deacetylase.

While the concentration range of the HDACi used will vary and will depend on the specific inhibitor. The concentration range may therefore be from about 0.001 nM to about 100 mM; preferably a range selected from one of the following: from about 0.01 nM to about 50 mM; from about 0.05 nM to about 10 mM; from about 0.1 nM to about 5 mM; from about 0.5 nM to about 1 mM; from about 1 nM to about 500 µM; from about 5 nM to about 250 µM; from about 10 nM to about 100 µM; from about 25 nM to about 50 µM.

Where artificial chromosome doubling is required in accordance with aspects and embodiments of the invention, suitable methods are taught in Antoine-Michard, S. et al., (1997) Plant cell, tissue organ cult., Cordrecht, the Netherlands, Kluwer Academic Publishers, 48(3): 203-207; Kato, A., Maize Genetics Cooperation Newsletter (1997) 36-37; and Wan, Y. et al., TAG (1989) 77: 889-892; and Wan, Y. et al., TAG (1991) 81: 205-211. Additional technical guidance for chromosome doubling is provided by Segui-Simarro J. M., & Nuez F. (2008) Cytogenet. Genome Res. 120: 358-369. Many procedures involve contact of plant cells with colchicine, anti-microtubule agents or anti-microtubule herbicides such as pronamide, nitrous oxide, or any mitotic inhibitor. The result is homozygous doubled haploid cells.

Where colchicine is used, the concentration in the medium may be generally 0.01%-0.2% or approximately 0.05% or APM (5-225 µM). The range of colchicine concentration may be from about 400-600 mg/L or about 500 mg/L.

Where pronamide is used the medium concentration may be about 0.5-20 µM. Examples of known mitotic inhibitors are listed below. Other agents such as DMSO, adjuvants or surfactants may be used with the mitotic inhibitors to improve doubling efficiency.

Common or trade names of suitable chromosome doubling agents include; colchicine, acetyltrimethylcolchicinic acid derivatives, carbetamide, chloropropham, propham, pronamide/propyzamide tebutam, chlorthal dimethyl (DCPA), Dicamba/dianat/disugran (dicamba-methyl) (BANVEL, CLARITY), benfluralin/benefin/(BALAN), butralin, chloralin, dinitramine, ethalfluralin (Sonalan), fluchloralin, isopropalin, methalpropalin, nitralin, oryzalin (SURFLAN), pendimethalin, (PROWL), prodiamine, profluralin, trifluralin (TREFLAN, TRIFIC, TRILLIN), AMP (Amiprofos methyl); amiprophos-methyl Butamifos, Dithiopyr and Thiazopyr.

The chromosome doubling agent may be contacted with an haploid embryo at various times. If the embryo is isolated the doubling agent may come in contact immediately after isolation. The duration of contact between the chromosomal doubling agent may vary. Contact may be from less than 24 hours, for example 4-12 hours, to about a week. The duration of contact is generally from about 24 hours to 2 days.

The invention is applicable to any angiosperm plant species, whether monocot or dicot.

Preferably, plants which may be subject to the methods and uses of the present invention are crop plants such as cereals and pulses, maize, wheat, potatoes, tapioca, rice, sorghum, millet, cassava, barley, pea, and other root, tuber or seed crops. Important seed crops are oil-seed rape, sugar beet, maize, sunflower, soybean, and sorghum. Other plants to which the present invention may be applied may include lettuce, endive, and vegetable brassicas including cabbage, broccoli, and cauliflower, and carnations, geraniums, tobacco, cucurbits, carrot, strawberry, sunflower, tomato, pepper, chrysanthemum.

Grain plants that provide seeds of interest and to which methods and uses of the invention can be applied include oil-seed plants and leguminous plants. These include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils and chickpea.

In particular, the invention is applicable to crop plants such as those including: corn (*Zea mays*), canola (*Brassica napus, Brassica rapa* ssp.), alfalfa (*Medicago sativa*), rice (*Oryza sativa*), rye (*Secale cerate*), sorghum (*Sorghum bicolor, Sorghum vulgare*), sunflower (*Helianthus annua*), wheat (*Triticum aestivum*), soybean (*Glycine max*), tobacco (*Nicotiana tabacum*), potato (*Solanum tuberosum*), peanut (*Arachis hypogaea*), cotton (*Gossypium hirsutum*), sweet potato (*Iopmoea batatus*), cassava (*Manihot esculenta*), coffee (*Coffea* spp.), coconut (*Cocos nucifera*), pineapple (*Ananas comosus*), citrus tree (*Citrus* spp.) cocoa (*Theobroma cacao*), tea (*Camellia senensis*), banana (*Musa* spp.), avocado (*Persea americana*), fig (*Ficus casica*), guava (*Psidium guajava*), mango (*Mangifer indica*), olive (*Olea europaea*), papaya (*Carica papaya*), cashew (*Anacardium occidentale*), macadamia (*Macadamia intergrifolia*), almond (*Prunus amygdalus*), sugar beets (*Beta vulgaris*), oats, barley, vegetables and ornamentals.

Similarly, the invention can be applied to perennial fast growing herbaceous and woody plants, for example trees, shrubs and grasses. A non-exhaustive list of examples of tree types that can be subjected to the methods and uses of the invention includes poplar, hybrid poplar, willow, silver maple, black locust, sycamore, sweetgum and *eucalyptus*. Shrubs include tobacco. Perennial grasses include switchgrass, reed canary grass, prairie cordgrass, tropical grasses, *Brachypodium distachyon*, and *Miscanthes*.

DH production is a major trait discovery and breeding tool, as described above. The HDACi compounds can be used to overcome two major bottlenecks in haploid embryo culture: induction of embryogenic divisions/embryos and conversion of embryos to seedlings.

The current best mode of the invention is a use of SAHA in *Brassica napus* microspores to achieve increased haploid embryogenesis and improved conversion of embryos into double haploid seedlings.

The inventors have also succeeded in achieving increased embryogenic divisions in immature male gametophytes of *Brassica rapa* and *Capsicum annuum* when exposing them to TSA In the description of experimental examples of the invention which follows, the following materials and methods were employed.

Plant Material and Culture

*Brassica napus* L. cv. Topas DH4079 and DH12075 were used as donor plants for microspore embryo culture. The *B. napus* plant growth and microspore isolation procedures were performed as described in Ousters, J. B. M. (2003) "Microspore culture in rapeseed (*Brassica napus* L.)" in: Doubled haploid production in crop plants: a manual, M. Maluszynski, K. J. Kasha, B. P. Forster, and I. Szarejko, eds (Dordrecht: Kluwer Academic Publishers), pp. 185-193.

Flower buds for microspore culture were grouped by size (measured from the tip of the flower bud to the bottom of the sepal), ranging from 3.0 to 3.5 mm for DH4079 and from 2.6 to 4.0 mm for DH12075. The microspores were isolated and cultured in NLN-13 medium (see Lichter, R. (1982) Mel. Plant 3: 594-602. For induction of embryogenesis, microspores were cultured in the dark at 33° C. for 20 hours, and subsequently transferred to 25° C. Non-induced microspore cultures were cultured continuously at 25° C. or 18° C. Trichostatin A (TSA, Sigma-Aldrich) was prepared in DMSO. Freshly isolated microspores were inoculated in medium containing TSA or the same volume of DMSO as a control. and cultured for 20 hours at the temperature indicated for each experiment. After this period the cultures were centrifuged at 200 g for 3 min, resuspended in fresh NLN-13 medium without TSA, and transferred to 25° C.

Arabidopsis flower buds at stage 11 were collected for anther culture. Flower buds were surface sterilized in 2% bleach for 10 minutes, then rinsed three times in distilled water. The anthers (without filament) were placed in liquid NLN-13 medium containing 0.5 µM ISA or the same volume of DMSO, and then cut in half transversely in the medium to release the microspores. The cultures were placed at 25° C. for 20 hours in the dark. The medium was then replaced by fresh NLN-13 medium by pipetting gently, and the cultures incubated at 25° C. for an additional four days. Free and loosely attached microspores were collected and stained with DAPI. Arabidopsis tide T-DNA insertion lines were obtained from Nottingham Arabidopsis Stock Centre. At least 300 microspores per sample were counted.

Reporter Lines

GFP-based reporter lines were generated for the Arabidopsis embryo-expressed genes, LEC1 (At1g21970; LEC1: LEC1-GFP) and GRP (At2g30560; GRP:GFP-GUS) and the B. napus ENODL4 gene (AB836663; ENODL4:GFP). For the LEC1:LEC1-GFP translational fusion, a 3110 bp DNA fragment comprising 1292 bp upstream of the translational start site and the entire coding region was amplified by PCR and recombined into pGKGWG using the Gateway cloning system (Invitrogen) according to the manufacturer's instructions. The Arabidopsis GRP gene encodes an EGG APPARATUS1-LIKE (EAL) protein (see Gray-Mitsumune, M., and Matton, D. P. (2006) Planta 223: 618-625) and is highly similar to a B. napus glycine-/proline-rich gene isolated from embryogenic microspore cultures (probe 563; see Joosen, R., et al, (2007) Plant Physiol. 144: 155-172). The Arabidopsis GRP:GFP-GUS transcriptional fusion was made by PCR amplifying a fragment comprising 861 bp upstream of the start codon and Gateway recombination into pBGWFS7,0. The BnENODL4 was identified as an early embryogenesis-expressed gene from B, napus microspore culture (Japanese Patent No. 35935650). A 1035 bp fragment of the promoter of BnENODL4 gene (GenBank accession no. AB098076) was cloned by inverse PCR, ligated to the 5'-end of an sGFP: nos terminator fragment and inserted into pBinKH, which is a modified version of a binary vector pGPTV-KAN (see Becker, D., et al. (1992) Plant Mol. Biol. 20: 1195-1197). The reporter constructs were transformed to Agrobacterium tumefaciens strain C5801 carrying the pMP90 Ti plasmid and then to B. napus DH12075 (see Moloney, M. M. et al. (1989) Plant Cell Rep. 8: 238-242) and/or Arabidopsis 0010 (see Clough, S. J., and Bent, A. F. (1998) Plant J. 16: 735-743).

Microscopy

The developmental stage and identity of cells in microspore and anther culture were visualized with the nuclear stain 4', 6-diamidino-2-phenylindole (DAPI, 1.25 µg/ml according to Ousters (2003) supra using a Zeiss Axioskop epifluorescence microscope with filter set no. 02. Approximately two hundred microspores or multicellular clusters were counted for each sample. GFP was imaged using confocal laser scanning microscopy (CLSM; Leica DM5500 Q). The GFP was excited with an argon laser line at 488 nm and detected with a 505-530 nm emission filter. Samples were counterstained with DAPI or propidium iodide (10 mg/ml; Sigma-Aldrich), Propidium iodide and red autofluorescence were excited at 532 nm and detected with a 620-660 nm emission filter. GFP and DAPI were covisualized with CLSM, For CLSM, DAPI was excited at 405 nm and detected with a 440-500 nm emission filter. The optical slices were median filtered with Leica LAS AF software. Arabidopsis anthers were cleared in HOG solution (water: Chloral hydrate: glycerol; 3:8:1) for 10 min, then observed under DIC microscopy with a Nikon OPTIPHOT microscope.

Molecular Analyses

Total RNA isolation and on-column DNase digestion were performed using the InviTrap Spin Plant RNA Mini Kit (Invitek) according to the manufacturer's instructions. For semi-quantitative RT-PCR, 250 ng of total RNA was used for first-strand cDNA synthesis with the Taqman Reverse Transcription Reagents Kit (Applied Biosystems). The cycling parameters were: one cycle at 98° C. for 30 s, 30 cycles comprising 98° C. for 5 s, 60° C. for 30 s, followed by 72° C. for 1 min. The semi-quantitative RT-PCR primers are from Malik et al. (2007) Plant Physiol. 144: 134-154. The quantitative RT-PCR primers for microarray validation were designed based on oligonucleotide probes from Affymetrix GeneChip® Brassica Exon 1.0ST Array (see Malik et al, (2007) supra and Love, C. G., et al. (2010) PloS one 5: e12812). The Arabidopsis hda T-DNA insertion lines were genotyped using the PCR primers. Microspore cultures for microarray analysis were cultured at 33° C. for eight hours with either TSA, cycloheximide (CHX, Sigma-Aldrich) dissolved in DMSO, DMSO or cycloheximide, or with TSA and cycloheximide together. The samples were harvested by centrifugation for total RNA was isolation, as described above. One microgram of total RNA from each sample was sent to the NASC Affymetrix Service for hybridisation to the Affymetrix Brassica Exon 1.0 ST GeneChip. Probe annotations were downloaded from Gene Expression Omnibus. The identifier for the annotation is GPL10733. The expression data was subjected to normalization using the RMA method from the 'affy' Bioconductor package. Log 2-transformed expression values were identified as differentially expressed using a Student's t-test. Multiple hypothesis testing correction was done using the Holm's method (Holm, S. (1979) Scandinavian Journal of Statistics 6: 65-70) implemented in the multtest's Bioconductor package. Mapman (see Thimm, O., et al. (2004) Plant J. 37: 914-939 was used to identify functional categories of differentially-expressed genes. The microarray data has been deposited to the Gene Expression Omnibus (GEO) database (GSE49070).

Immunochemistry

Freshly isolated microspores and microspores cultured for 8 hours under different experimental conditions were harvested by centrifugation. Proteins were extracted by boiling in SDS-sample buffer (30 µl per ml of culture) and electrophoresed in a Midget 12.5% SDS-PAGE gel under reducing conditions. After transfer of the proteins to PVDF membrane and blocking with 5% milk powder in PBS, 0.1% Tween 20, the blots were incubated for 2 hours with primary antibody (1:2000 dilution). The primary antibodies used in this study are as follows: anti-acetyl-Lysine (ICP0380; ImmuneChem Pharmaceuticals), anti-Histone H3 (ab1791; Abcam), anti-Histone H4 (clone 62-141-13; Millipore), and anti-acetyl-Histone H3 and anti-acetyl-Histone H4 (Millipore). Secondary goat anti-rabbit-HRP antibody (Sigma) was used in a 1:2000 dilution and signals were detected by using enhanced chemiluminescence (SuperSignal West Femto Chemiluminescent Substrate, Pierce).

Example 1—TSA Induces Hyperproliferation in Poorly Responsive B. napus Genotype, DH12075

Cultured microspores and pollen of B. napus genotype, DH12075 were treated with the HDAC inhibitor, TSA. We examined the development of microspore cultures by staining heat-stressed (hereafter referred to as control) and heat-stressed plus TSA-treated immature male gametophytes at different developmental stages with the nuclear dye, DAPI. Initial dosage experiments were used to establish the minimal exposure time (20 h) in relation to the specific phenotypes discussed below.

FIG. 1. Effect of the duration of TSA treatment on sporophytic cell division in B. napus DH12075 microspore culture. Immature male gametophytes from two different bud sizes (black bars and white bars) were cultured in the presence of 0.5 µM TSA or with the equivalent volume of DMSO (control) at 33° C. Sporophytic cell divisions were counted after DAPI staining after five days of culture. Treatments for longer than 20 hours did not further enhance or reduce the proportion of sporophytic divisions.

Figure 2:
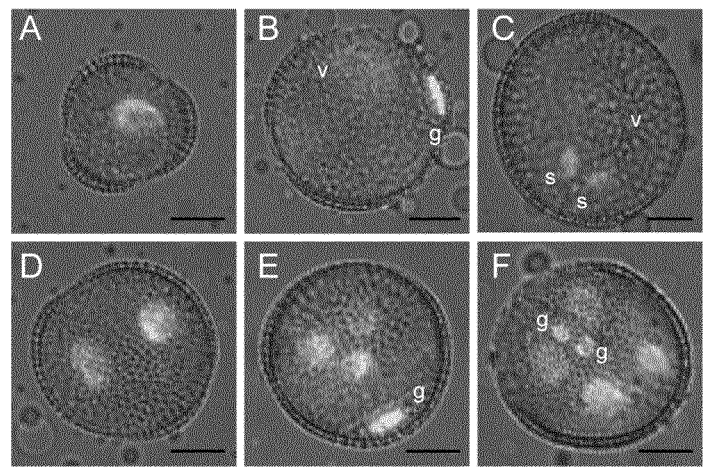
FIG. 2 panels A-F are micrographs of gametophytic (A-C) and sporophytic structures from *B. napus* microspore culture, as described in Example 1. Panels G and H are bar charts of data showing the percentage of different cell types observed in control (G) and TSA-treated cultures (H) at different times, also as described in Example 1.

FIG. 2 shows the effect of TSA on early cell division patterns in B. napus microspore culture. DAPI-stained gametophytic (A-C) and sporophytic structures (D-F) are present in the first two days of microspore culture, (A)=microspore, (B)=binucleate pollen, (C)=trinucleate pollen, (D)=sporophytically-divided cell with two diffusely-stained vegetative-like nuclei. (E)=sporophytic structure with three vegetative-like nuclei and one condensed, generative-like nucleus. (F)=multinucleate sporophytic structure with four vegetative-like nuclei and two generative-like nuclei, (G-H) =the percentage of different cell types observed in control (G) and TSA-treated cultures (H). The cell types were grouped into the following categories: dead gametophytes (white bars); gametophytic structures at the microspore (light grey bars); binucleate (medium grey bars) and trinucleate (dark grey bars) stages; and sporophytically-divided structures (black bars). Control, DMSO treated sample. Immature male gametophytes were obtained from donor flower buds that were grouped by size. The samples are ranked from youngest to oldest (1-6) based on the developmental stages of the male gametophytes found in each donor bud size group. V=vegetative(-like) nucleus; g=generative(-like) nucleus; s=sperm nucleus. Scale bar=10 µm.

Figure 2G:
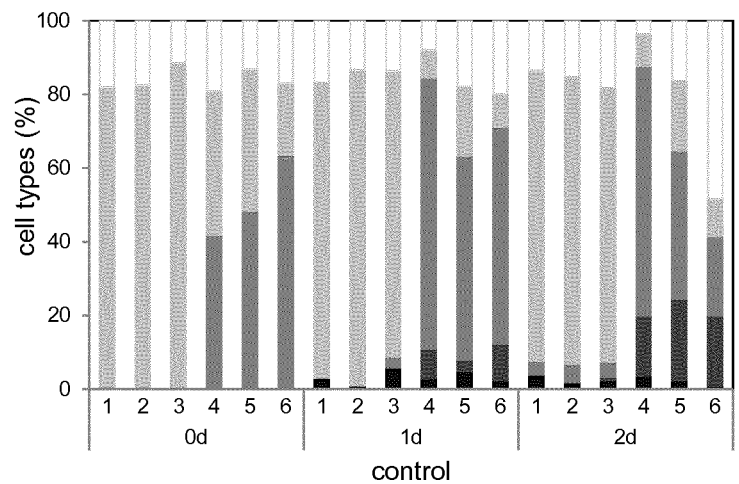

After two days of heat stress, immature male gametophytes in control cultures arrest, continue pollen development, or divide sporophytically. Male gametophyte development in culture follows the same course of development as in the anther (see FIGS. 1A-C). The single-celled microspore divides asymmetrically (pollen mitosis I, PM I) to generate a pollen grain with a large vegetative cell containing a diffuse nucleus and a smaller generative cell with a more compact nucleus. The vegetative cell arrests in GIGO, while the generative cell divides once more (pollen mitosis II, PM II) to produce the two gametes, the sperm cells, that participate in double fertilisation. Microspores that divide sporophytically contain two large, diffusely-stained nuclei, rather than the large, diffusely-stained vegetative nucleus and small condensed generative nucleus produced after PM I (FIG. 2D). Immature gametophytes that divide sporophytically after PM I, which is rarely (<1%) observed in control cultures from this genotype, contain a small generative-like cell in addition to the larger sporophytic cells (FIG. 2E). After heat stress treatment, the majority of the cells in the control culture were gametophytic-like or had died, as evidenced by the lack of DAPI staining (FIG. 2G). Approximately 6% of the population divided sporophytically in the first two days of cultures, producing cell clusters with two to six nuclei. The developmental stage of the starting population in the control cultures did not influence the initial proportion of cells that divided sporophytically.

Figure 2H:
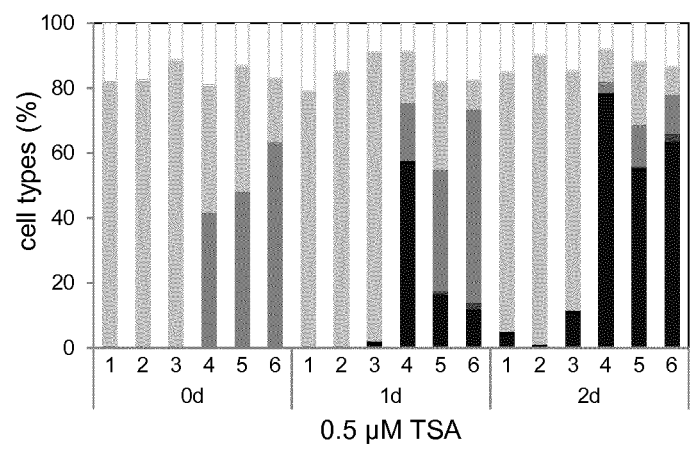

The combined effect of heat stress and 0.5 µM TSA on sporophytic cell division after two days of culture was dramatic, with up to 80% of the population dividing sporophytically (FIG. 2H). The largest increase in the proportion of sporophytically-divided structures was observed in cultures that initially contained binucleate pollen. The majority of sporophytically-divided cells cultures contained two to six diffusely-stained nuclei, as in control cultures. Unlike control cultures, approximately 10% of the sporophytically-divided cells also contained one or more generative-like nuclei (FIG. 2F). The low frequency of cells with generative-like nuclei is surprising considering the 40 to 60% binucleate pollen that was present at the start of culture. The generative nucleus may degrade, or may assume a more diffuse morphology, perhaps contributing to the observed ectopic divisions.

The observations indicate that loss of HDAC activity in cultured immature male gametophytes induces a high frequency of ectopic sporophytic cell division. HDAC proteins appear to play a major role in controlling cell cycle progression during male gametophyte development. The combined effect of heat-stress and TSA treatment is more potent than that of heat-stress alone, both in terms of the developmental stages and the proportion of immature gametophytes that are induced to divide sporophytically.

Example 2—TSA and Heat-Stress Induce Similar Developmental Changes

The developmental fate of heat-stressed control cultures and cultures exposed to both heat-stress and ISA was followed by examining older cultures in more detail. Initial experiments showed that the proportion of dividing cells, as well as their developmental fate was influenced by the concentration of TSA that was applied to the culture. Heat-stressed microspores and pollen were treated with a range of TSA concentrations and the cultures examined after five and 15 days using DAPI staining to characterize the different multicellular structures that developed.

Figure 3:
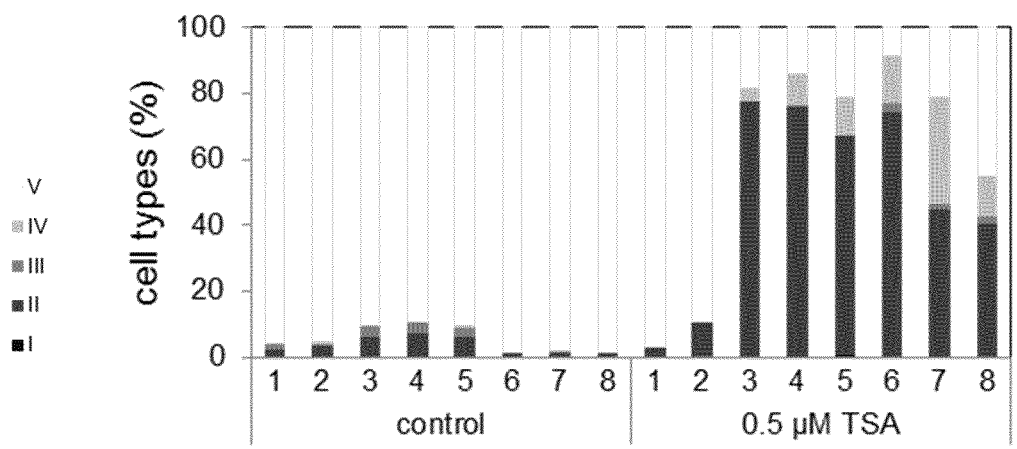
FIG. 3 panel A is a bar chart showing the effect of TSA on sporophytic growth in *B. napus* microspore culture as described in Example 2. Panels B G are micrographs of type I-IV sporophytic structures after five (B-E) and 15 (F-G) days of culture, as described in Example 2.
Figure 3:
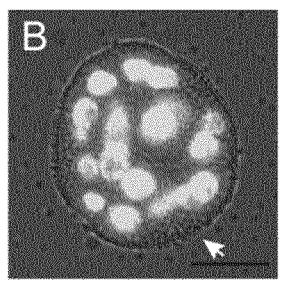
Figure 3:
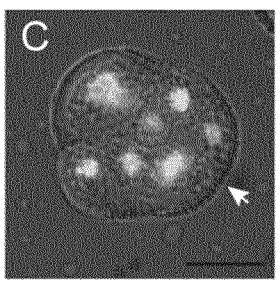
Figure 3:
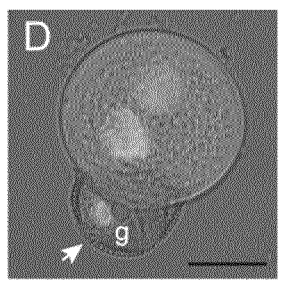
Figure 3:
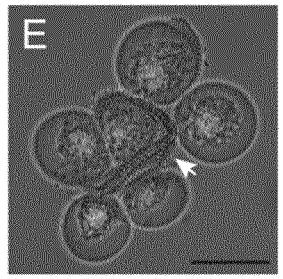
Figure 3:
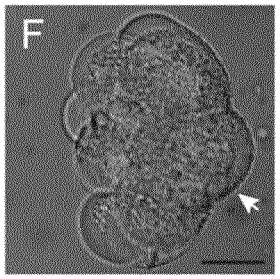
Figure 3:
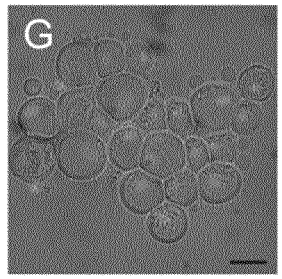

FIG. 3 shows the effect of TSA on sporophytic growth in B. napus microspore culture. (A)=percentage of cells that had divided gametophytically (white bars) or sporophytically (grey bars) after five days of microspore culture. The corresponding structures are shown in FIG. 3 B-E (has scale bar of 20 µm) where FIG. 3(B-G) shows images of type I-IV sporophytic structures after five (B-E) and 15 (F-G) days of culture. The sporophytic cell clusters are categorized as follows: Type I, classical embryo-forming structures (black bars, FIG. 3B); Type II, compact callus-like structures (dark grey bars, FIG. 3C); Type extruded sporophytic structures (medium grey, FIG. 3D) and Type IV, loose callus-like structures (light grey bars, FIG. 3E), Type II structure (FIG.

3F) and Type IV structure (FIG. 3G). Dead microspores and pollen were not included. Control is a DMSO treated sample. Nuclei in Figures B-G are stained with DAPI. Arrow shows intact (B) or broken (C, D, E, F) exine. The developmental stages of the starting material (1-8) are ranked from youngest to oldest.

Four types of sporophytic structures were distinguished in five-day old control cultures (FIG. 3B-E), some of which have been previously described in microspore cultures of other *Brassica* genotypes. Type 1 structures are the classical embryo-forming structures that are routinely observed in microspore culture. After five days of culture these multicellular structures contained up to 40 nuclei that were still enclosed in the pollen wall (exine; FIG. 3B). Cell walls were formed in Type I structures, but were not clearly visible. These embryogenic multicellular structures were only observed in control cultures that initially contained a mixture of late uninucleate microspores and early binucleate pollen; and only comprised a small proportion of the population of dividing cells (0,5%), Type II structures were the most abundant structures present in five day control cultures. They are callus-like; less compact than Type I structures, and contain up to five cells that had already started to emerge from the exine (FIG. 3C). Type III structures contained two to three large and diffusely-stained nuclei and were no longer enclosed by the exine, which remained attached to the cell clusters and was often associated with a generative-like nucleus (FIG. 3D), Type IV structures, which were rarely observed in control cultures, comprised loose callus-like clusters with DAPI stained cell walls (FIG. 3E).

The same sporophytic structures as in the control were observed in five day old cultures that received a combined heat-stress and TSA-treatment, but in different proportions depending on the concentration of TSA that was applied (FIG. 3A).

Figure 4:
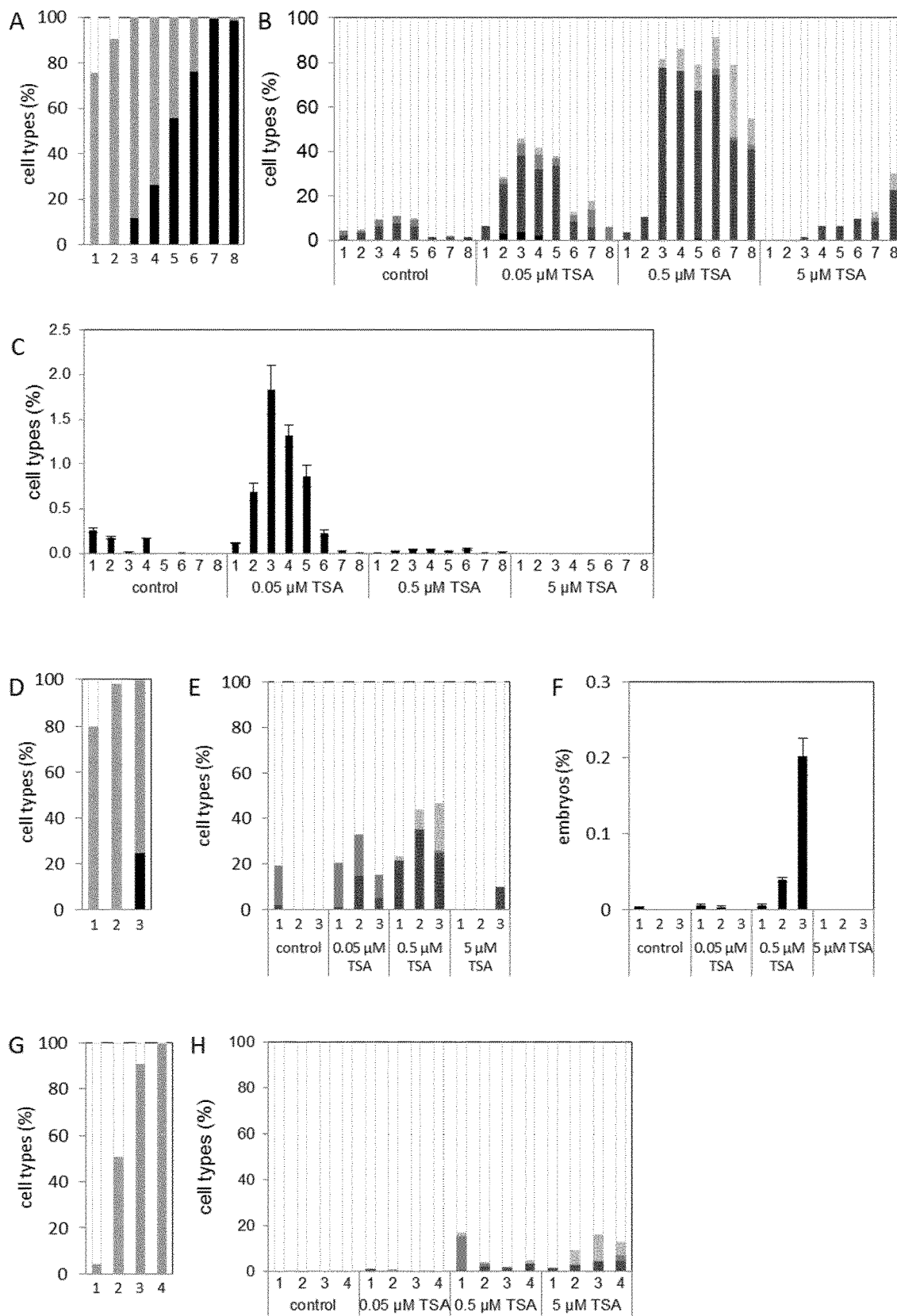
FIG. 4 shows a series of bar charts (A-H) with data showing the effect of TSA and culture temperature on cell division and embryo formation in *B. napus* microspore culture, as described in Example 2.

FIG. 4 shows the effect of ISA and culture temperature on cell division and embryo formation in *B. napus* microspore culture. Microspores and immature pollen from different bud sizes were cultured in the presence of different concentrations of ISA compared with the equivalent volume of DMSO (control) at three temperatures: A–D=33° C., D–F=25° C., G–H=18° C. For each treatment, the samples are ranked from left to right along the z-axis according to the developmental stage of the microspores and pollen, A, D, G shows developmental stage of microspores and pollen at the start of culture in the experiments in A=33° C., D=25° C. and G=18° C. The microspores and pollen were categorized as follows: mid-uninucleate microspore (white bars); late-uninucleate microspore (grey bars) and binucleate pollen (black bars) stages. B, E, H shows the effect of TSA on cell division in *B. napus* microspore embryo culture. The percentage of cells that divided gametopyhytically or sporophytically after five days of microspore culture at B=33° C., E=25° C., H=18° C. The sporophytic cell clusters were examined after five days of culture and categorized as follows: Type I, classic embryogenic structures (black bars); Type II, compact callus-like structure (dark grey bars); Type III, extruded sporophytic structures (medium grey bars) and Type IV, loose callus-like structure (light grey bars). Gametophytic cell types are indicated by white bars. Dead microspores and pollen were not counted. C, F show embryo yield from microspores and pollen formed in the presence of DMSO (control) or different concentrations of TSA at C=33 CC or F=25° C. Histodifferentiated embryos did not develop in control and TSA-treated samples that were cultured at 18° C. (data not shown).

Treatment with heat-stress and TSA mainly induced the formation of Type II (up to 77% versus 7% in the control cultures) and Type IV structures (up to 32% versus 0.5% in the control cultures). Type I classical embryogenic structures were observed at a low frequency when 0.5 µM TSA was added to the culture medium (up to 1% versus 0,5% in the control cultures), but were much more abundant when a ten times lower concentration of TSA was used (see FIG. 4B).

With the exception of Type III structures, all of the sporophytic multicellular structures observed in control and heat-stress plus TSA-treated cultures were still present and had increased in size after 15 days of culture, and were still more abundant in TSA-treated cultures (FIG. 3F, G). Types II and IV cell clusters eventually stopped growing and died. A very small percentage of heart to cotyledon stage embryos were observed in the control cultures (up to 0.3%). Fewer embryos were produced in heat-stressed cultures treated with 0.5 TSA (up to 0.05%), but were up to five times more abundant than in control cultures when heat-stressed cultures treated with the lower concentration (0.05 µM) of TSA (FIG. 4C). Both the control and heat-stress plus TSA-treated cultures contained classical type I embryogenic structures and their numbers can easily account for all the embryos formed; however, we cannot rule out that other types of cell clusters, such as the Type II callus-like structures, also develop into histodifferentiated embryos.

We determined whether the heat-stress treatment used to induce haploid embryogenesis is required for the TSA cell proliferation phenotype. Microspore cultures incubated at temperatures lower than 33° C. divide sporophytically, with the proportion of dividing cells depending on the culture temperature and stage of male gametophyte development, but produce fewer or no embryos compared to 33° C. cultures. An increased percentage of sporophytic divisions appeared when TSA was applied to microspore cultures growing at either 18 or 25° C. (FIG. 4D-H), as well as a corresponding increase in embryo production at 25° C. Up to 0.2% embryo production was observed in TSA-treated cultures compared to practically no embryo production in the non TSA-treated controls (FIG. 4F). Higher TSA concentrations were needed to induce cell proliferation and embryo production at these lower temperatures compared to cultures grown at 33° C.

Whilst not wishing to be bound to any particular theory, the inventors consider that TSA and heat-stress mediate similar developmental changes in microspore culture.

Example 3—Sporophytic Cell Clusters are Embryogenic

The cell clusters that are formed in heat-stressed, TSA treated cultures resemble those found in control cultures that are only exposed to a heat-stress treatment. They include classical embryogenic structures, as well as structures that have been classified as non-embryogenic based on their unorganized structure, early release from the exine, and the lack of a protoderm, which is known to considered a hallmark for commitment to embryo development in culture. Semi-quantitative RT-PCR and GFP reporter lines were used to determine whether the different types of sporophytic structures that develop in control and TSA-treated cultures are embryogenic.

The expression of four embryo-expressed transcription factors genes, BABY BOOM (BBM); LEAFY COTYLEDON1 (LEC1); LEC2 and FUSCA3 is known to be positively correlated with the embryogenic potential of *B. napus* microspore cultures. Semi-quantitative RT-PCR analysis showed that expression of these four genes was enhanced when microspore cultures were treated with TSA, regardless of the culture temperature (data not shown) suggesting that TSA treatment is sufficient to activate the embryo pathway in microspore culture.

B. napus GFP reporter lines were then developed for two Arabidopsis embryo-expressed genes, LEC1 (LEC1:LEC1-GFP) and GLYCINE-RICH PROTEIN (GRP, GRP:GFP-GUS), to identify the specific structures that contribute to the enhanced embryo gene expression observed in TSA-treated cultures. The early embryo expression of both GFP reporters was confirmed in B. napus zygotic embryos, where LEC1 expression was detected as early as the 2-cell stage and GRP expression from the zygote stage onward (data not shown). Neither gene was expressed during the uni-, bi- or trinucleate stages of male gametophyte development, either in the anther, or in microspore cultures grown at 18° C. to promote pollen development.

Figure 5:
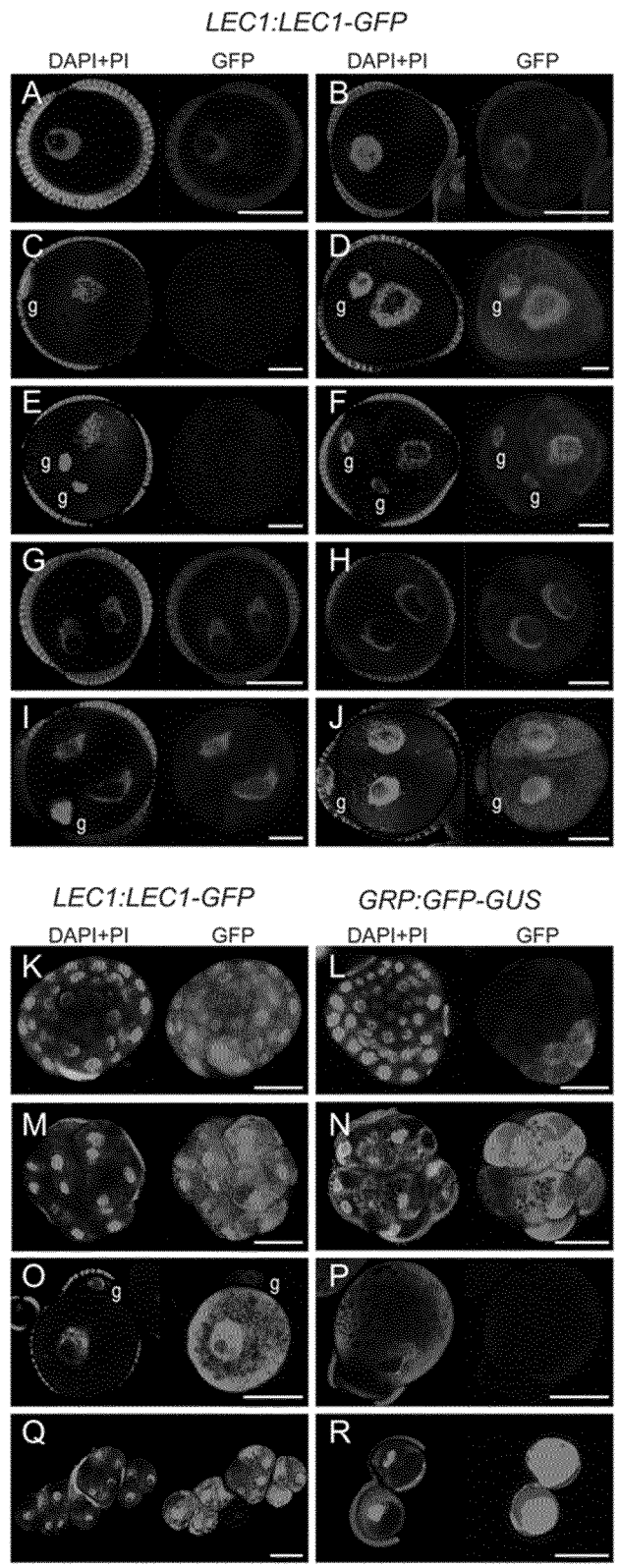
FIG. 5 shows micrographs of embryo-expressed GFP reporters in *B. napus* microspore culture, as described in Example 3.

The predominately nuclear localisation of the LEC1-GFP fusion was used to more precisely follow the developmental identity of the different cell types found in microspore cultures within the first three days of culture. FIG. 5 shows micrographs of embryo-expressed GFP reporters in B. napus microspore culture (g=generative-like nucleus; scale bar in (A–J)=10 µm, (K–R)=25 µm). Panels A-H show expression of LEC1:LEC1-GFP in two day-old control (A, C, E, G) and TSA-treated (B, D, F, H, I, J) cultures. Panels (A, B) show microspore-like structure; (C, D) binucleate pollen-like structure; (E, F) trinucleate pollen-like structure; (G, H) sporophytically-divided structure; (I) sporophytically-divided binucleate pollen-like structure showing GFP in the two vegetative-like nuclei, but not in the generative-like nucleus; (J) sorophytically-divided binucleate pollen-like structure showing GFP in both the two vegetative-like nuclei and the generative-like nucleus; (K-R) LEC1:LEC1-GFP and GRP:GFP-GUS expression in five to eight day-old TSA-treated microspore cultures treated with TSA; (K and L) Type I embryogenic structures at eight days; (M and N) Type II compact callus-like structures at eight days; (0 and P) Type III extruded sporophytic structures at five days; (Q and R) Type IV loose callus-like structure at eight days. For each panel, the image on the left side of each panel shows the GFP fluorescence and the image on the right side, the fluorescence from DAPI staining.

In control (heat-stressed) microspore cultures, LEC1-GFP was expressed in microspore-like structures, and in cells that contained two large, diffusely stained nuclei, but not in bi- or trinucleate pollen-like structures (FIG. 5A, C, E, G). After TSA treatment of heat-stressed microspores, LEC1-GFP was also observed in the same structures as in the control cultures, but also in bi- and trinucleate pollen-like structures (FIG. 5B, D, F, H). In pollen-like structures, LEC1-GFP was expressed in either the vegetative-like nucleus or in both the vegetative- and generative-like nuclei, but never in generative-like nuclei alone (FIGS. 5I and J).

Both the LEC1 and GRP reporters were expressed in the classical embryo (Type I) structures in the same spatial pattern as in zygotic embryos (FIGS. 5K and L), as well as throughout the Type II and IV sporophytic structures. Only LEC1 expression was detected in Type III structures. The same pattern of expression was observed after TSA-treatment in older cultures (FIG. 5M-R), An overview of the LEC1 and GRP expression patterns in control and TSA-treated cultures (data not shown) suggests that TSA-treated and control microspore cultures show similar developmental changes. Surprisingly, microspores can be reprogrammed to embryo development following heat-stress/TSA treatment in the absence of cell division. Simultaneous exposure to TSA and heat-stress gives stronger effect than heat-stress alone, in that the embryo program is also activated in both the vegetative- and generative-like cells of immature gametophyte.

Example 4—TSA Induces Totipotency in Arabidopsis Immature Male Gametophytes

Figure 6:
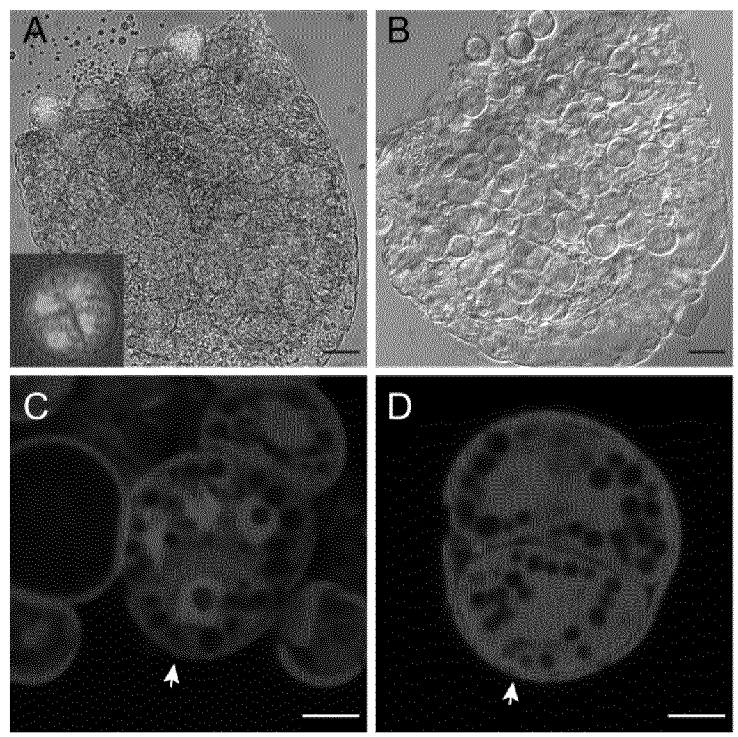
FIG. 6 shows micrographs of five day-old anther cultures, as described in Example 4.

Multicellular structures that resemble the Type II and IV structures seen in Brassica microspore culture are produced when stage 11 Arabidopsis anthers are cultured at 25° C. with 0.5 µM TSA. FIG. 6 shows micrographs of five day-old anther cultures (scale bar (A, B)=50 µm, (C, D)=10 µm). TSA induces embryogenic cell divisions in Arabidopsis immature male gametophytes. Panels show: (A)=DAPI stained anther in TSA-treated culture showing, multicellular, sporophytic structures derived from immature male gametophytes (arrow). The insert shows a DAPI-stained multicellular structure with four nuclei. (B)=cleared anther from a control culture showing lack of spoorphytic cell proliferation. (C)=expression of LEC1:LEC1-GFP and (D)=ENOD4L:GFP in a Type II compact callus-like structure in TSA-treated anthers. The exine still surrounds the sporophytic structures (marked by arrows).

Growth of donor plants at a low temperature and in vitro culture at a higher temperature, as in B. napus was not necessary, nor did it improve the production of sporophytic structures. The percentage of immature male gametophytes that divided sporophytically in cultured Col0 anthers was highly variable (0-5%), but was never observed in anthers cultured without TSA (FIG. 6B). Expression of the LEC1 and GRP marker lines in TSA treated cultures was examined, but only LEC1 expression was detected (FIG. 6C). However, a third embryo reporter ENOD4-LIKE:GFP (ENOD4L:GFP) was expressed in the ISA-induced multicellular structures (FIG. 6D). TSA therefore also induces embryogenic growth in Arabidopsis immature male gametophytes.

Example 5—Behaviour of Hda and Rbr Mutants in Arabidopsis Anther Culture

Arabidopsis contains 18 HDAC genes (referred to as HDA1-18) grouped into the Rpd3/Hda1, HD-tuin and sirtuin families. This experiment determined whether T-DNA insertions in Arabidopsis HDAC genes phenocopy TSA-treated anthers. Lines with T-DNA insertions in Rpd3/HDA1 and HD-twin type HDA genes were examined for ectopic divisions of the male gametophyte during normal anther development in situ, but did not show any changes in the pollen cell division pattern in these lines.

Figure 7:
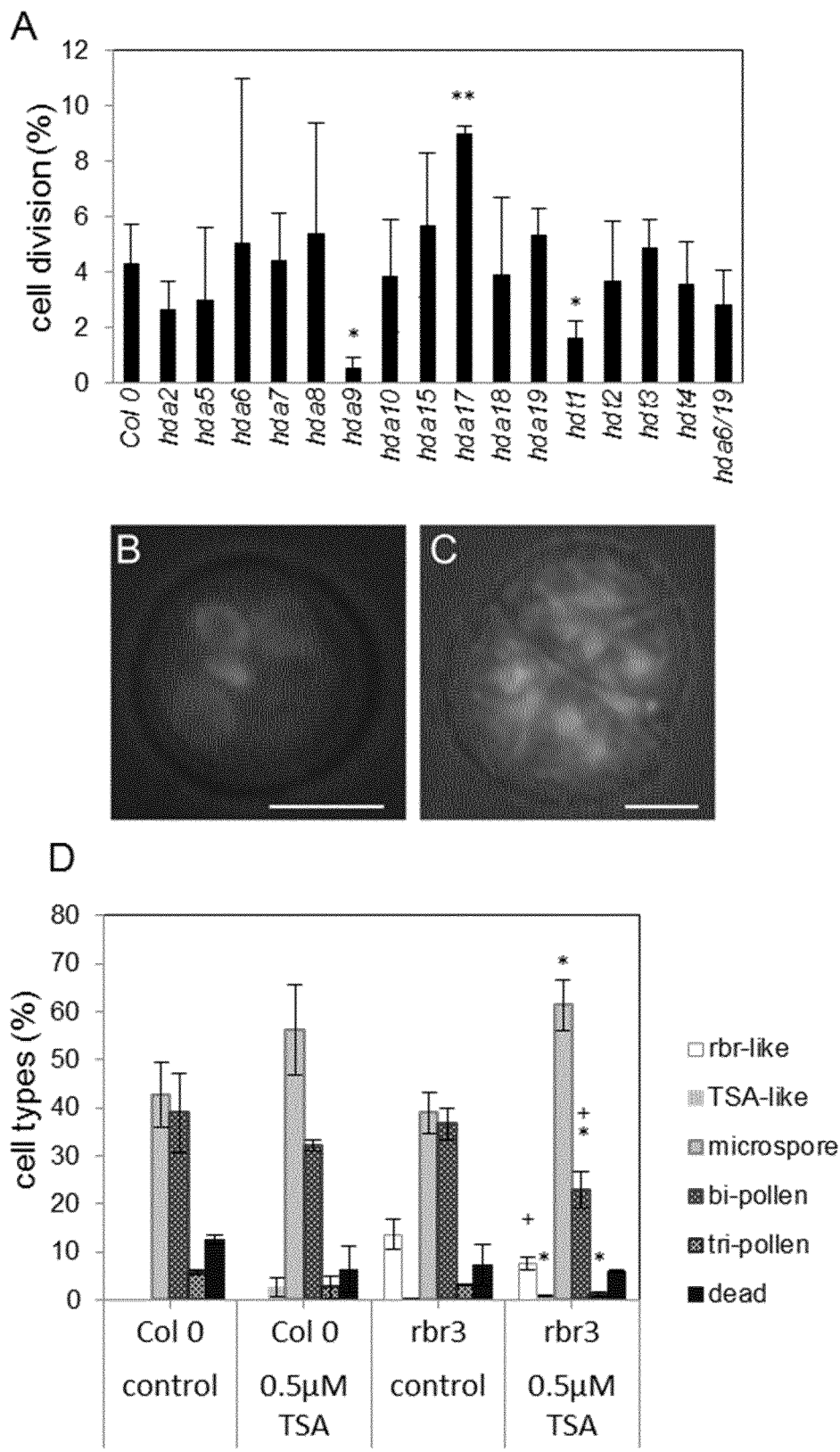
FIG. 7 shows bar charts (A, D) and micrographs (B, C) showing behaviour of hda and rbr mutants in *Arabidopsis* anther culture, as described in Example 5.

FIG. 7 (scale bar=10 µm) shows behaviour of hda and rbr mutants in Arabidopsis anther culture. The panels are as follows: (A)=shows the efficiency of sporophytic cell division in immature male gametophytes of cultured anthers from hda T-DNA insertion lines treated with 0.5 µM TSA. Statistical comparison (Student's T-test) was made between the TSA-treated 0010 anthers and the ISA-treated hda mutant anthers, *p<0.05; **p<0.01; (B, C)=multicellular sporophytic structures observed in cultured rbr-3/+ anthers, rbr-like multicellular structure with three vegetative-like cells and one generative-like cell (B) and Type II multicellular structure with eight nuclei (C); (D)=relative proportion of the different types of cells observed in rbr3/+ anther cultures treated with 0.5 µM TSA or DMSO (control cultures). Samples were analysed five days after the start of culture. Statistically significant differences were observed between the response of TSA treated and untreated rbr-3 anthers (*, p<0.05; Student's T-test) and TSA treated rbr-3 and 0010 anthers (+, p<0.05; Student's T-test).

It is currently difficult to test for TSA-independent or TSA hypersensitive responses in the single hda insertion lines due to the low and variable response of the culture system. Given these limitations, none hda insertion lines showed sporophytic divisions in cultured pollen in the absence of TSA; however, when the same anthers were cultured in the presence of TSA, the hda17 T-DNA insertion line showed a small, but significant increase in the percentage of sporophytic cell divisions relative to the control (FIG. 7A). This data suggests that the activity of at least one HDAC, HDA17, is required to suppress ectopic cell divisions in *Arabidopsis* pollen.

Experiments were done to see whether RBR plays a role in TSA-mediated cell totipotency. Homozygous rbr mutants are gametophytic lethal, therefore the experiments were performed on heterozygous rbr anthers (rbr-3/+), which contain 50% rbr pollen. The developing structures were scored as dead, gametophytic, rbr-like or TSA-like. The rbr phenotype is most penetrant during the bicellular stage of pollen development and is characterized by structures with multiple vegetative cells, and to a lesser extent, extra generative-like cells (FIG. 7B). The TSA phenotype differs from that of rbr in that the TSA-like cells are larger, contain more vegetative-like cells, and have a stretched or broken exine (FIG. 7C). If an RBR-HDAC interaction is required to prevent sporophytic cell divisions in culture, then culturing rbr mutant pollen without TSA could induce TSA-like divisions. Culture of rbr-3 anthers with TSA should not have an additive effect on the percentage of sporophytic divisions, except when TSA inhibition of HDAC activity is incomplete. Ectopic cell proliferation of immature male gametophytes was observed when rbr-3/+ anthers were cultured in the absence of TSA. The typical compact rbr-like structures with up to 6 nuclei that develop in planta were observed (FIG. 7D). Strikingly, rbr-3/+ anthers cultured in the absence of TSA also produced a low percentage (0,5%) of enlarged and loosely-connected Type II multicellular structures (FIG. 7D), which was never observed in cultured control anthers from wild-type plants. No differences were observed between TSA-treated wild-type and TSA-treated rbr-3/+ anthers, other than the typical rbr-like divisions that are observed in the rbr3 line; however, compared to untreated rbr-3/+ anthers, TSA-treated rbr-3/+ anthers showed a decrease in the frequency of rbr-like divisions.

These experiments with cultured rbr3/+ anthers show that a loss of RBR function is sufficient to induce the formation of embryogenic cell clusters in *Arabidopsis* anther culture in the absence of TSA. The decrease in the frequency of rbr-like divisions after TSA treatment may reflect a requirement for HDAC activity in promoting the typical rbr-type cell-cycle progression.

Example 6—TSA Promotes Histone Acetylation

An acetylated lysine antibody was used in combination with protein gel blotting to identify proteins whose acetylation status changes in 8 hour heat-stress plus TSA-treated *B. napus* microspore cultures compared to heat-stressed control cultures.

Figure 8:
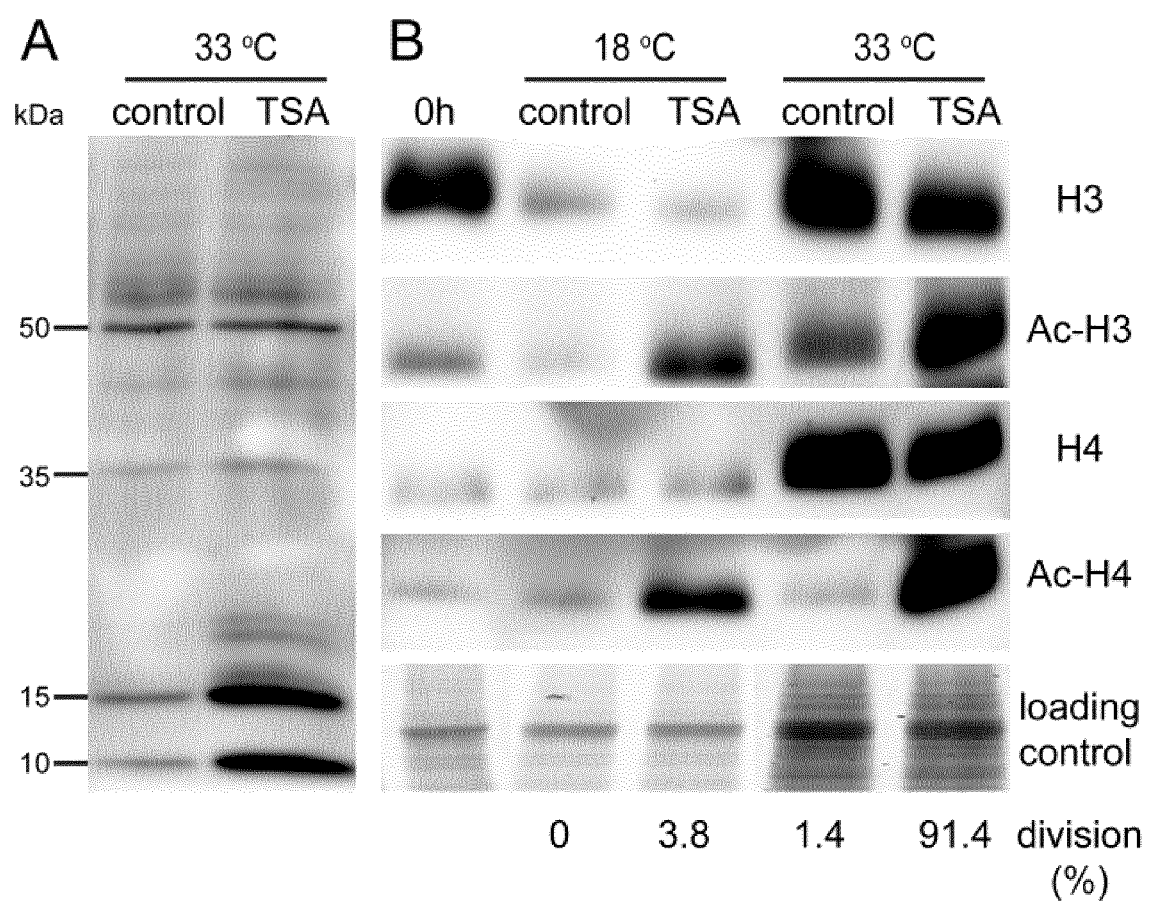
FIG. 8 is a photograph of Western blots as described in Example 6.

FIG. 8 shows that TSA enhances histone acetylation. Panels show: (A)=Western blot of total acetylated proteins in microspore cultures treated for eight hours with DMSO (control) or TSA-proteins in the range of 10-25 kDa are differentially acetylated after TSA treatment compared to the control; (B)=Western blot of total and acetylated (Ac) histone H3 and H4 in microspore cultures treated for eight hours with DMSO (control) or TSA. The percentages of sporophytic divisions in the different cultures at day 5 are shown under each sample.

Increased protein acetylation was observed in small molecular weight proteins in the range of 10-25 kDa in the TSA treated cultures compared to control cultures (see FIG. 8A). The acetylation status of histones H3 and H4 was determined during microspore culture using acetylated histone H3 (Ac-H3) and H4 (Ac-H4) antibodies. Microspore cultures were started from buds containing mostly binucleate pollen and placed for eight hours at either 18° C. or 33° C. with or without 0.5 μM ISA. As expected, TSA greatly enhanced sporophytic divisions at 18° C. and 33° C. compared to the untreated controls (FIG. 8B). Although this increase in cell division had no clear effect on the total amount of histone H3 and H4 detected in the control and TSA-treated cultures, the level of histone H3 and H4 acetylation increased dramatically in the ISA-treated cultures relative to control cultures, both at 18° C. and at 33° C. (FIG. 8B).

The main effect of decreased HDAC activity following TSA treatment in microspore culture appears to be increased acetylation of histones.

Example 7—Effect of HDAC Inhibitors on Sporophytic Cell Division in Microspore Cultures of *B. napus* DH 12075

Figure 9:
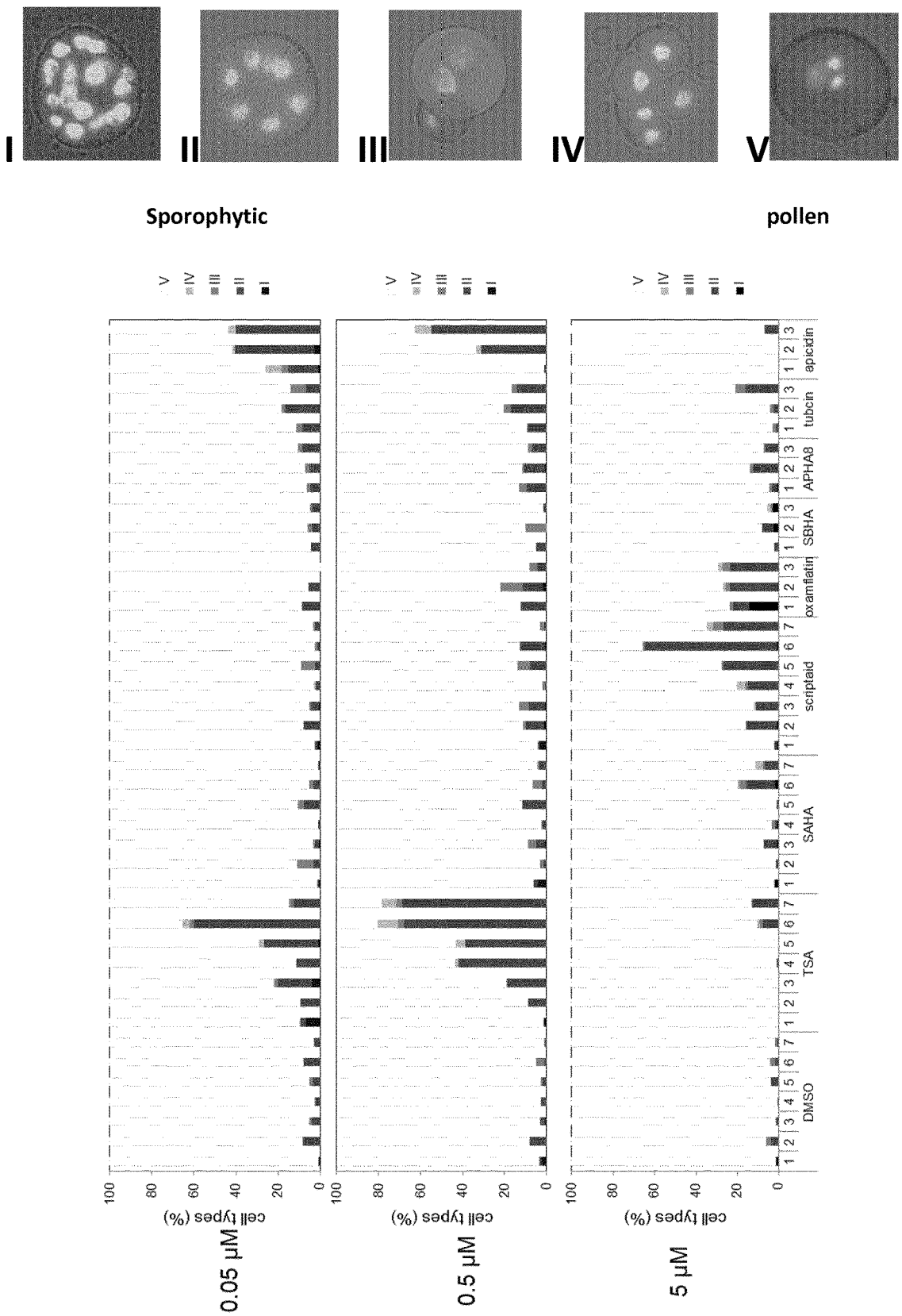
FIG. 9 shows data of the effects of various HDACi on sporophytic cell division in microspore cultures of *B. napus* DH 12075; at three different concentrations compared to DMSO control.

FIG. 9 shows data for sporophytic cell divisions from microspores and pollen in the presence of DMSO (control) or different concentrations of HDAC inhibitors after 5 days of microspore culture, Seven different populations of microspores/pollen were tested and are ranked from (left to right) the developmentally youngest to the developmentally oldest stages.

As shown in FIG. 9, I=Type I, classical embryo-forming structures (black bars); II=Type II, compact callus-like structures (dark grey bars) III=Type III, extruded sporophytic structures (medium grey bars), IV=Type IV, loose callus-like structures (light grey bars) and V=pollen (white bars, F). Dead microspores and pollen were not included. Control is a DMSO treated sample. The corresponding structures (I-V) are shown on the side panel.

Example 8—Effect of HDAC Inhibitors on Embryo Yield in Microspore Cultures of *B. napus* DH 12075

Figure 10:
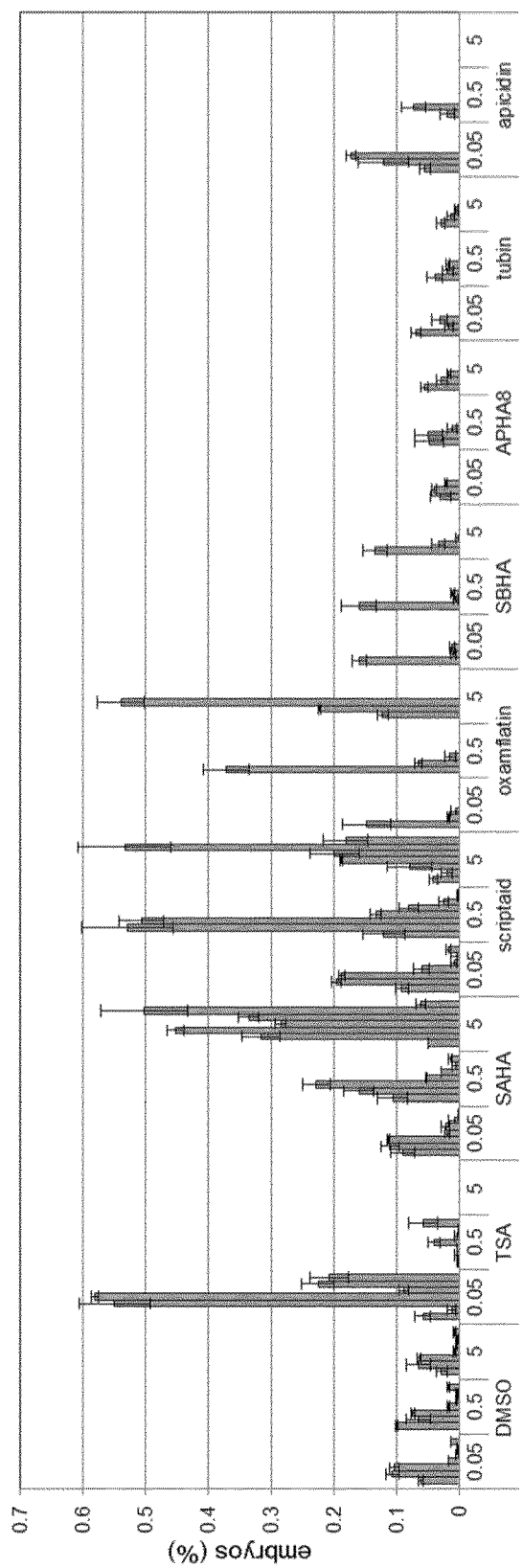
FIG. 10 shows data of the effects of HDACi on embryo yield in microspore cultures of *B. napus* DH 12075.

FIG. 10 shows the embryo yield from microspores and pollen formed in the presence of DMSO (control) or different concentrations of HDAC inhibitors after 15 days of microspore culture. Seven different populations of microspores/pollen were tested and are ranked (left to right) from the developmentally youngest to the developmentally oldest stages.

Example 9—HDACi Improve Embryo Quality in Older Stages of Donor Pollen

Figures 11A, 11B:
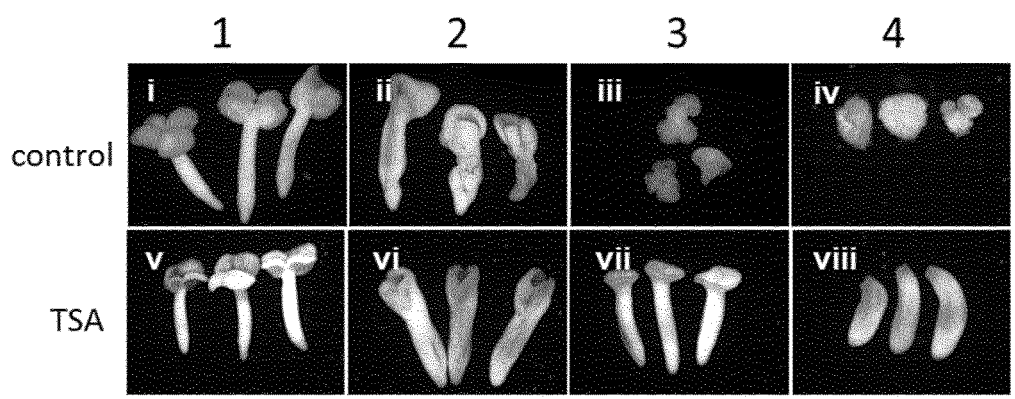
FIG. 11 shows data demonstrating how HDACi improve embryo quality in older stages of donor pollen.

FIG. 11 shows data for microspore cultures from four stages of development treated with either DMSO (control) or HDACi and scored for the morphological type of embryo that was formed, as well as the yield of embryos. The four different cultures (1-4) are ranked from (left to right) the developmentally youngest to the developmentally oldest stages. FIG. 11A shows the schematic representation of the different types of embryo found in the four different cultures and at each concentration. Each embryo represents a yield of 0.1%. Each of the different types of embryo was formed almost exclusively at the indicated stage/concentration. FIG. 11B shows the types of embryo are: normal (i, v), rough (ii, vi), compressed (iii), ball-shaped (iv), cup-shaped cotyledons (vii) and reduced cotyledons (viii). For any given stage, at an optimum concentration HDACi treatment improves both the yield and the quality of the embryos that are formed relative to the control.

Example 10—HDACi-Treated Embryos can be Readily Converted to Seedlings

Figure 12:
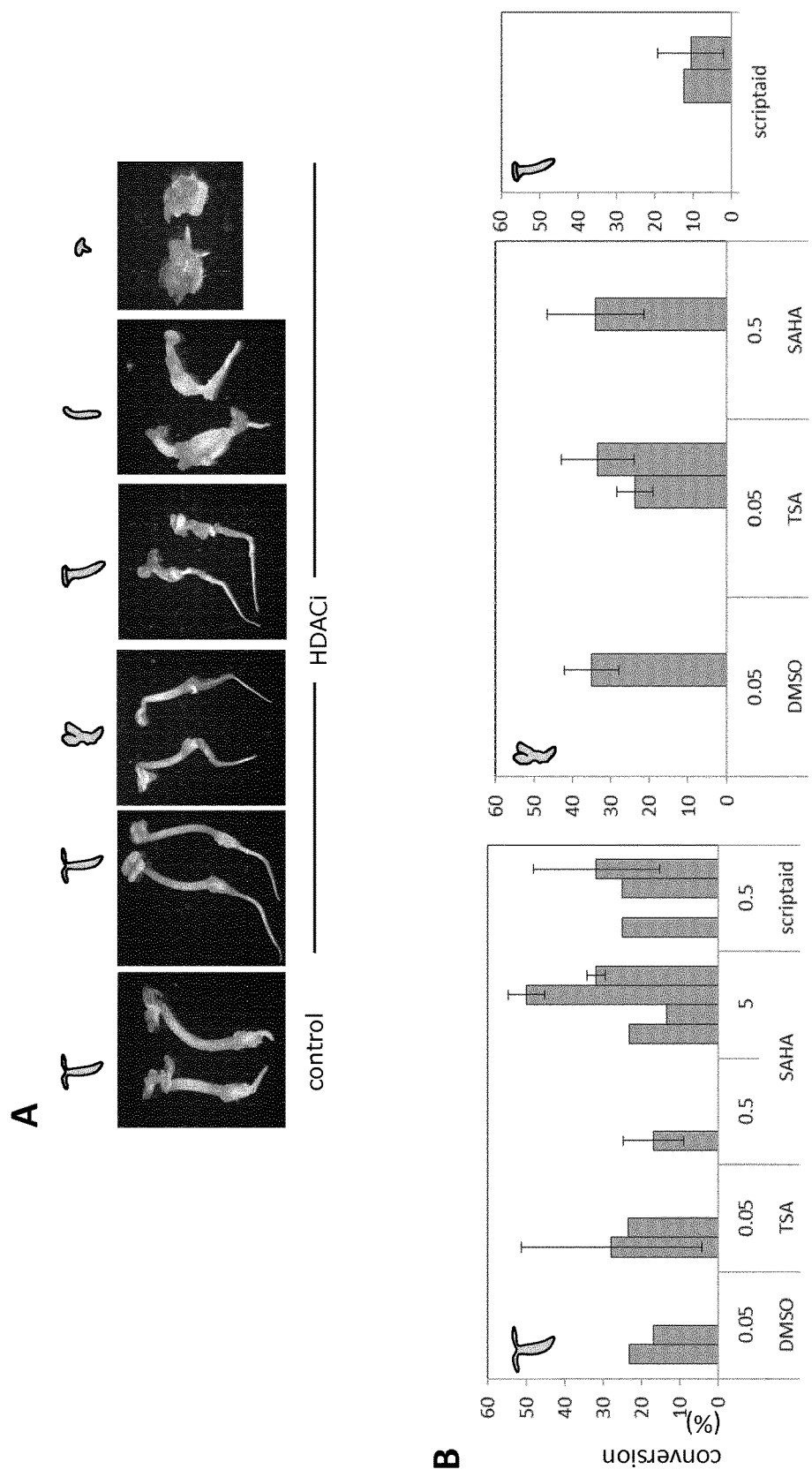
FIG. 12 shows data demonstrating how HDACi-treated embryos can be readily converted to seedlings.
Figure 13:
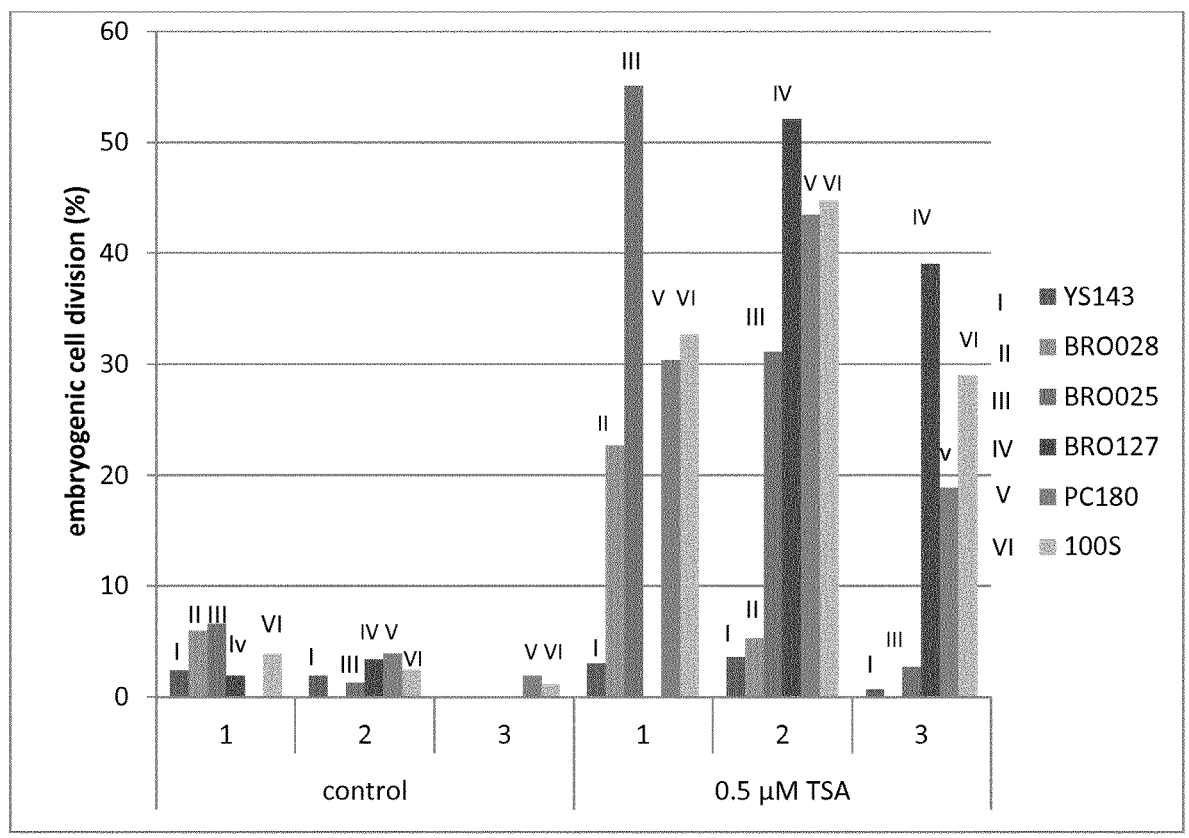
FIG. 13 shows data exemplifying how genotype influence degree of TSA enhanced embryogenesis in Brassica rapa.
Figure 14:
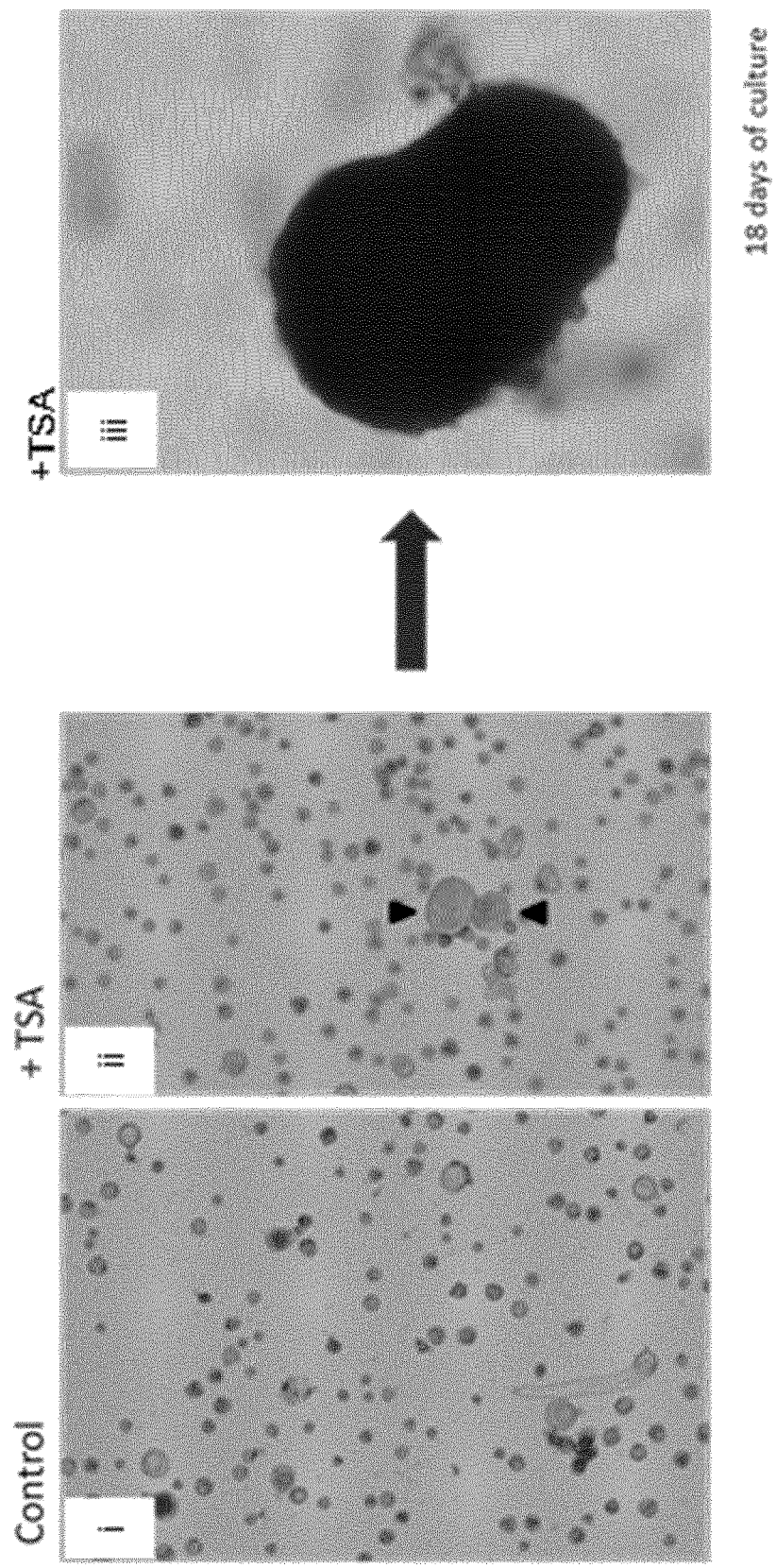
FIG. 14 consists of micrographs showing the effect to TSA-treated (ii) and control (i) microscope culture embryo development in a recalcitrant (non-responsive) genotype of Brassica oleracea Gongylodes group (kohlrabi), (iii) is an enlargement of a large embryo at 18 days.
Figure 15:
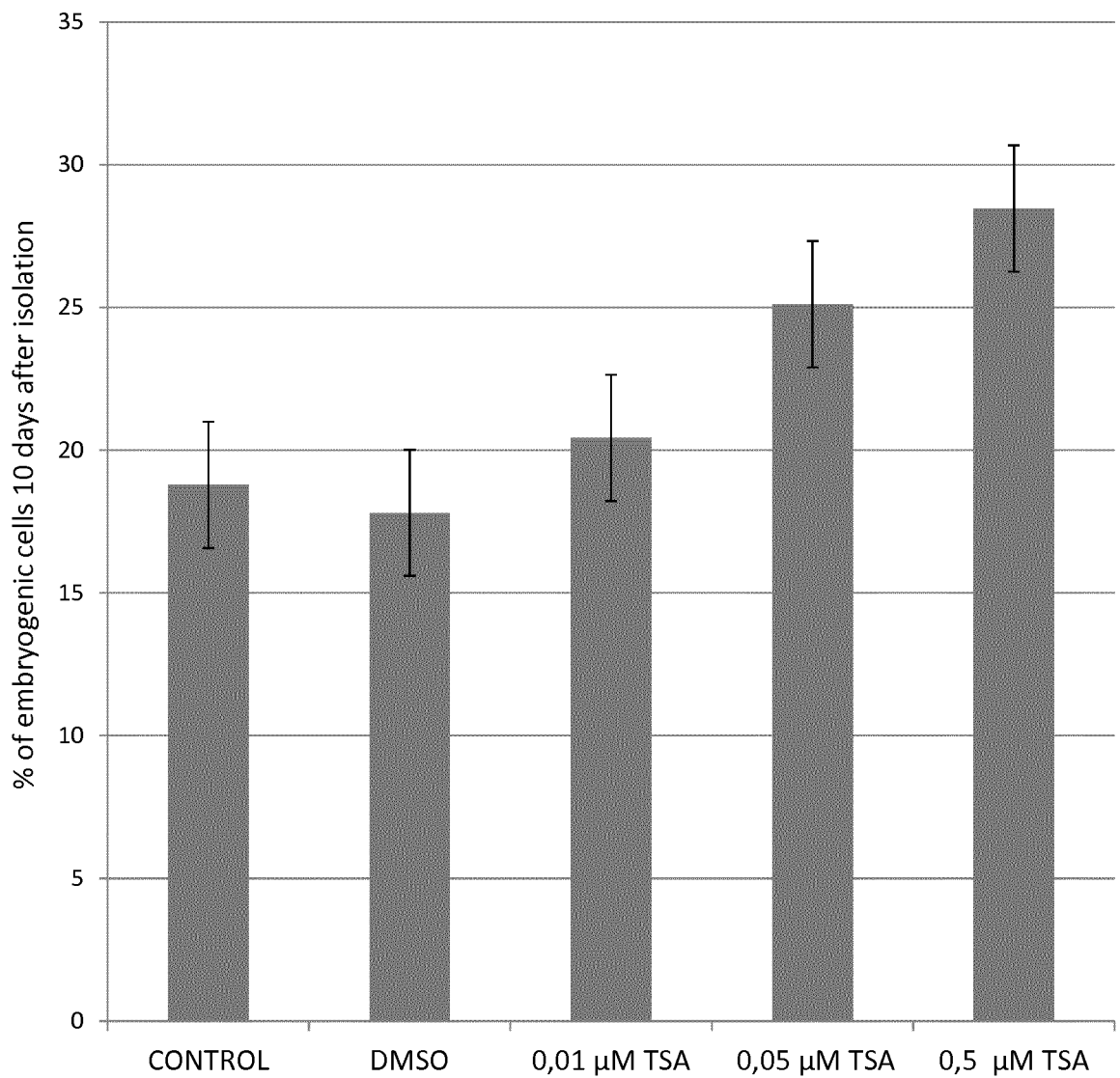
FIG. 15 shows data on percentage of embryogenic microspores in 10 day-old control and TSA-treated Capsicum annuum microscope cultures.
Figure 16:
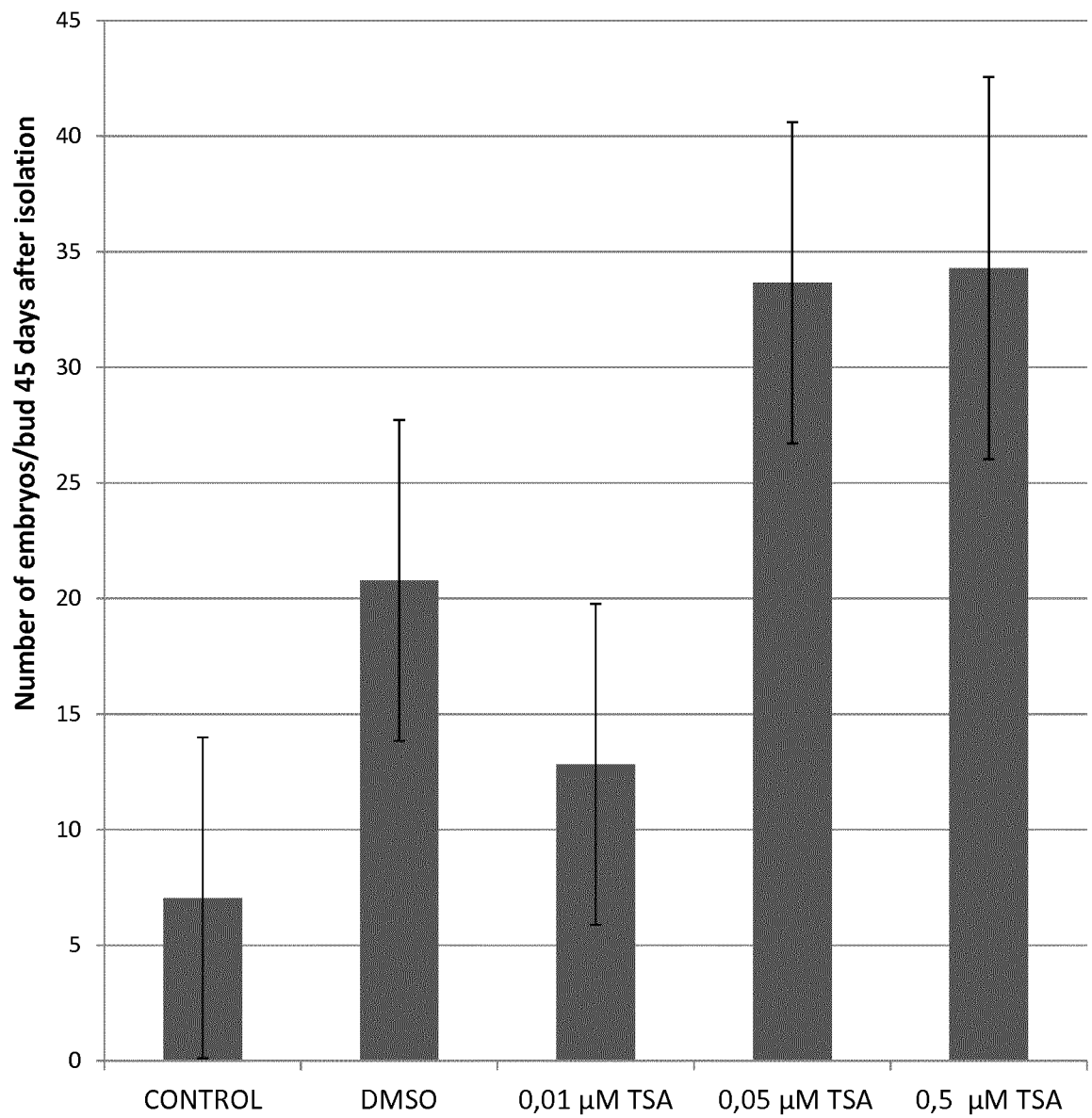
FIG. 16 shows data a number of embryos obtained per bud used in 45 days day-old control and TSA-treated Capsicum annuum microscope cultures.

FIG. 12A shows the different morphological types of embryos produced in culture, whether from control or HDACi-treated cultures were able to produce roots when transferred to germination medium, with the exception of the ball-shaped type of embryo. All of the embryos that produced roots, except for the short embryo type, initiated root development from the root meristem, as evidenced by the development of roots within a few days of growth on germination medium. However, short embryos still produced roots, but much later, indicating that the roots were produced indirectly via a callus phase. Notably, root growth in HDACi treated embryos was more vigorous than in the similar type of control embryos (compare first two panels).

In FIG. 12B, different types of embryos derived from different populations of microspores/pollen treated with DMSO (control) or different concentrations of HDACi were transferred to regeneration medium and evaluated for their ability to produce shoots (measure of conversion). Embryos derived from HDACi-treated cultures showed similar or improved (SAHA) germination compared to the control.

The invention claimed is:

1. A method of producing a haploid plant embryo comprising culturing or growing haploid plant material in the presence of a hydroxamic acid compound, wherein the hydroxamic acid compound is chosen from trichostatin A, suberoylanilide hydroxamic acid, suberoyl bis-hydroxamic acid, scriptaid, oxamflatin, tubacin, APHA Compound 8, and apicidin.

2. The method of claim 1, wherein the hydroxamic compound has histone deacetylase inhibitor activity.

3. The method of claim 1, wherein the hydroxamic acid compound has haploid embryogenesis activity.

* * * * *